US006207842B1

(12) United States Patent
Romanczyk, Jr. et al.

(10) Patent No.: US 6,207,842 B1
(45) Date of Patent: Mar. 27, 2001

(54) PROCESS FOR PREPARING PROCYANIDIN (4-6 OR 4-8) OLIGOMERS AND THEIR DERIVATIVES

(75) Inventors: Leo J. Romanczyk, Jr., Hackettstown; Alan P. Kozikowski, Princeton, both of NJ (US); Werner Tueckmantel, Washington, DC (US)

(73) Assignee: Mars Incorporated, McLean, VA (US)

( * ) Notice: Subject to any disclaimer, the term of this patent is extended or adjusted under 35 U.S.C. 154(b) by 0 days.

(21) Appl. No.: 08/948,226

(22) Filed: Oct. 9, 1997

(51) Int. Cl.$^7$ .................................................. C07D 311/26
(52) U.S. Cl. ............................................ 549/399; 549/400
(58) Field of Search .................................... 549/354, 355, 549/350, 381, 386, 385, 396, 398, 399, 400, 406, 407

(56) References Cited

FOREIGN PATENT DOCUMENTS 0096007   12/1983  (EP) .

OTHER PUBLICATIONS

J.J. Botha et al., "Synthesis of Condensed Tannins. Part 4. A Direct Biomimetic Approach to [4,6]–and [4,8]–Biflavanoids", *J. Chem. Soc., Perkin Trans. I*, 1235–1245 (1981).
J.J. Botha et al., "Synthesis of Condensed Tannins. Part 5. The First Angular [4,6:4,8]–Triflavanoids and Their Natural Counterparts", *J. Chem. Soc., Perkin Trans I*, 527–533 (1982).
H. Kolodziej, "Synthesis and Characterization of Procyanidin Dimers as Their Peracetates and Octamethyl Ether Diacetates", *Phytochemistry* 25, 1209–1215 (1986).
H. Van Rensburg et al., "The First Enantioselective Synthesis of Trans–and Cis–Dihydroflavonols", *J. Chem. Soc., Chem. Commun.*, 24: 2747–2746 (1996).
K. Toshima et al., "Recent Progress in O–Glycosylation Methods and Its Application to Natural Products Synthesis", *Chem. Rev.*, 93, 1503–1531 (1993).
D. Kahne et al., "Glycoslation of Unreactive Substrates", *J. Am. Chem. Soc.*, 11, 6881–6882 (1989).
M. Funayama et al., "A New Microorganism Producing a Glucosyl Transfer Enzyme to Polyphenols", *Biosci. Biotech Biochem.*, 58, (5) 817–821 (1994).
K. Igarashi, "The Koenigs–Knorr Reaction", *Adv. Carbohydrate Chem Biochem.*, 34, 243–283 (1997).
D.B. Dess et al., "A Useful 12–I–5 Triacetoxperiodinane (The Dess–Martin Periodinane) for the Selective Oxidation of Primary or Secondary Alcohols and a Variety of Related 12–I–5 Species", *J. Am. Chem. Soc.*, 113, 7277–7287 (1991).
R.E. Ireland et al., "An Improved Procedure for the Preparation of the Dess–Martin Periodinane", *J. Org. Chem.*, 58, 2899 (1993).
S.D. Meyer et al., "Acceleration of the Dess–Martin Oxidation by Water", *J. Org. Chem.*, 59, 7549–7552 (1994).

Jacobus A. Steenkamp et al., "Stereospecific Functionalization of the Heterocyclic Ring Systems of Flavan–3–ol and [4,8]–Biflavan–3–ol Derivatives with 2,3–Dichloro–5,6–Dicyano–1,4–Benzoquinone (DDQ)", *Tetrahedron Letters*, vol. 26, No. 25, pp. 3045–3048, (1985).
L. Yeap Foo et al., "Condensed Tannins: Synthesis of the First 'Branched' Procyanidin Trimer", *J. Chem. Soc., Chem. Commun.*, 1984, pp. 85–86.
Klaus Weinges et al., "Synthese Des Octamethyl–Diacetyl–Procyanidins B3" *Chem. Ber.*, 103, 2344–2349 (1970).
Haruo Kawamoto et al., "Syntheses of Condensed Tannin Derivatives Regiospecifically Linked Through a Single Interflavanoid–Linkage and Their Protein–Precipitating Capacities", *Mokuzai Gkkaishi*, vol. 37, No. 8, pp. 741–747 (1991).
Haruo Kawamoto et al., "Chemical Structure of Synthetic Condensed Tannin From Benzylated Flavan–3,4–Diol", *Mokuzai Gkkaishi*, vol. 37, No. 5, pp. 488–493 (1991).
E. Kiehlmann et al., "Iodination and Deuteration of Catechin Derivatives", *Can. J. Chem.*, 66, pp. 2431–2439 (1988).
M.–C. Pierre, et al., "Deuterium Labeled Procyanidin Synthesis," *Tetrahedron Letters*, 38, pp 5639–5642 (1997).
S. Miura et al., "Synthesis of [3–$^2$H]–and [3–$^3$H]–Cianidanol," *Radioisotopes*, 32 (5), pp 225–230 (1983).
Creasy, L.L. et al., "Structure of Condensed Tannins," *Nature*, 208, 1965, pp. 151–153.
Delcour, J.A. et al., "Synthesis of Condensed Tannins. Part 9. The Condensation of Sequence of Leucocyanidin with (+)–Catechin and with resultant Procyanidins," *J. Chem. Soc. Perkin. Trans.*, 1983, pp. 1711–1717.
Eastmond, R., "The Separation of a Dimer of Catechin occurring in Beer," *J. Inst. Brew.*, vol. 80, No. 2 (Mar./Apr. 1974), pp. 188–192.
Gramshaw, J.W., "Phenolic constituents of beer and brewing materials. II. The Role of Polyphenols in the Formation of Non–Biological Haze," *J. Inst. Brew.*, vol. 73, No. 5 (Sep./Oct. 1967), pp. 455–472.
Hundt, H., et al., "Synthesis of Condensed Tannins. Part 3," *J.C.S. Perkin I* (1981), pp. 1227–1234.
Miura, S. et al., *Chem. Abstr.*, 1983, 99, 158183r.
Nonaka, G. et al., "Tannins and Related Compounds," *Chem. Pharm. Bull.*, 35(1), pp. 149–155, 1987.

(List continued on next page.)

*Primary Examiner*—Christopher Henderson
(74) *Attorney, Agent, or Firm*—Margaret B. Kelley; Clifford Chance Rogers & Wells, LLP

(57) ABSTRACT

A process is disclosed for the production of polyphenol oligomers having n polyphenol monomers, n being an integer from 2–18. The process includes coupling of a protected polyphenol, having protected phenolic hydroxyl groups, with a C-4 functionalized polyphenol monomer. The protected polyphenol may be a protected polyphenol monomer or a protected polyphenol oligomer having 2–17 monomers. Advantageously, polyphenol monomers forming the polyphenol oligomers may be the same or different.

17 Claims, 4 Drawing Sheets

OTHER PUBLICATIONS

Romanczyk, Jr., et al., "Antineoplastic cocoa extracts and methods for making and using the same," U.S. Pat. No. 5,554,645 (issued Sep. 10, 1996).

Schlama, T. et al., "Total Synthesis of Halomon," *Angew. Chem. Int. Edgl.,* 1998, 37, pp. 2085–2087.

Roux, D.G., et al., "The Direct Biomimetic Synthesis, Structure and Absolute Configuration of Angular and Linear Condensed Tannins," *Chem. Org. Natural,* 41, 1981, pp. 48–76.

Swain, T., "Leucocyanidin," *Chemistry and Industry,* 1954, pp. 1144–1145.

PROCESS FOR PREPARING PROCYANIDIN (4-6 OR 4-8) OLIGOMERS AND THEIR DERIVATIVES

CROSS-REFERENCE TO RELATED APPLICATIONS

Reference is made to U.S. application Ser. No. 08/831,245, filed Apr. 2, 1997, Ser. No. 08/709,406, filed Sep. 6, 1996, U.S. Pat. No. 6,015,913, Ser. No. 08/631,661, filed Apr. 2, 1996, ABN and Ser. No. 08/317,226, filed Oct. 3, 1994 (now U.S. Pat. No. 5,554,645) and PCT/US96/04497, each of which is incorporated herein by reference.

FIELD OF THE INVENTION

This invention relates to synthetic polyphenol oligomers and methods for making and using the same.

Documents cited in this disclosure pertain to the field of this invention, and each document cited herein is hereby incorporated herein by reference.

BACKGROUND OF THE INVENTION

Polyphenols are a highly diverse group of compounds (Ferreira, D., Steynberg, J. P., Roux, D. G. and Brandt, E. V., *Tetrahedron*, 48, (10), 1743–1803 (1992)) which widely occur in a variety of plants, some of which enter into the food chain. In some cases they represent an important class of compounds for the human diet. Although some of the polyphenols are considered to be non-nutritive, interest in these compounds has arisen because of their possible beneficial effects on health.

For instance, quercetin (a flavonoid) has been shown to possess anticarcinogenic activity in experimental animal studies (Deschner, E. E., Ruperto, J., Wong, G. and Newmark, H. L., *Carcinogenesis*, 7, 1193–1196 (1991) and Kato, R., Nakadate, T., Yamamoto, S. and Sugimura, T., *Carcinogenesis*, 4, 1301–1305 (1983)). (+)-Catechin and (−)-epicatechin (flavan-3-ols) have been shown to inhibit Leukemia virus reverse transcriptase activity (Chu S.-C., Hsieh, Y.-S. and Lim, J.-Y., *J. of Natural Products*, 55, (2), 179–183 (1992)). Nobotanin (an oligomeric hydrolyzable tannin) has also been shown to possess anti-tumor activity (Okuda T., Yoshida, T., and Hatano, T., Molecular Structures and Pharmacological Activities of Polyphenols— Oligomeric Hydrolyzable Tannins and Others—Presented at the XVIth International Conference of the Groupe Polyphenols, Lisbon, Portugal, Jul. 13–16, 1992). Statistical reports have also shown that stomach cancer mortality is significantly lower in the tea producing districts of Japan. Epigallocatechin gallate has been reported to be the pharmacologically active material in green tea that inhibits mouse skin tumors (Okuda et al., Ibid.). Ellagic acid has also been shown to possess anticarcinogen activity in various animal tumor models (Boukharta M., Jalbert, G. and Castonguay, A., Efficacy of Ellagitannins and Ellagic Acid as Cancer Chemopreventive Agents—Presented at the XVIth International Conference of the Groupe Polyphenols, Lisbon, Portugal, Jul. 13–16, 1992). Proanthocyanidin oligomers have been patented by the Kikkoman Corporation for use as antimutagens. The use of phenolic compounds in foods and their modulation of tumor development in experimental animal models has been recently presented at the 202nd National Meeting of The American Chemical Society (Phenolic Compounds in Foods and Their Effects on Health I, Analysis, Occurrence & Chemistry, Ho, C.-T., Lee, C. Y., and Huang, M.-T editors, ACS Symposium Series 506, American Chemical Society, Washington, D.C. (1992); Phenolic Compounds in Foods and Their Effects on Health II. Antioxidants & Cancer Prevention, Huang, M.-T., Ho, C.-T., and Lee, C. Y. editors, ACS Symposium Series 507, American Chemical Society, Washington, D.C. (1992)).

However, none of these reports teaches or suggests cocoa extracts or compounds therefrom, any methods for preparing such extracts or compounds therefrom, or, any uses as described in U.S. application Ser. No. 08/831,245 filed Apr. 2, 1997.

Isolation, separation, purification, and identification methods have been established for the recovery of a range of procyanidin oligomers for comparative in vitro and in vivo assessment of biological activities. For instance, anti-cancer activity is elicited by pentameric through decameric procyanidins, but not by monomers through tetrameric compounds. Currently, gram quantities of pure (>95%) pentamer are obtained by time-consuming methods which are not satisfactory for obtaining a sufficient quantity of the pentamer for large scale pharmacological and bioavailability studies. Even greater effort is required to obtain gram quantities of higher oligomers, hexamers through dodecamers, for similar studies since they are present in the concentration in the natural product are much lower than the pentamer. Additionally, increasing oligomeric size increases structural complexity. Factors such as the chirality of the monomer units comprising the oligomer at different interflavan linkage sites, dynamic rotational isomerization of the interflavan bonds, and the multiple points of bonding at nucleophilic centers pose efficiency constraints on current analytical methods of separation and purification for subsequent identification.

These collective factors point to a need for synthesis methods to not only permit the unambiguous proof of both structure and absolute configuration of higher oligomers, but also to provide large quantities of structurally defined oligomers for in vitro and in vivo assessment. Such synthesis methods would lead to the creation of multiple configurational oligomers, some identical to those found in nature, as well as rare or "unnatural" types. Accordingly, it would be advantageous to develop a versatile synthetic process capable of providing large quantities of any desired polyphenol oligomer.

OBJECTS OF THE INVENTION

It is an object of the present invention to provide a method of synthesizing polyphenols and derivatives thereof.

It is another object of the present invention to provide a method of synthesizing an oligomeric compound of the formula $A_n$, wherein A is a monomer having the formula:

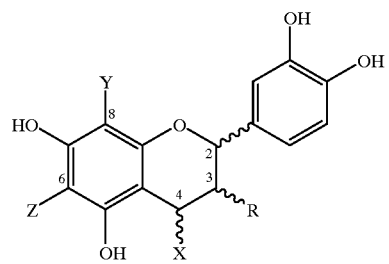

wherein
  n is an integer from 2 to 18, and higher;
  a bond to carbon position 2 has alpha or beta stereochemistry;

a bond to carbon position 3 has alpha or beta stereochemistry;

a bond to carbon position 4 has alpha or beta stereochemistry;

R is hydrogen, hydroxyl, an O-glycoside, a substituted O-glycoside, OC(O)-aryl, substituted OC(O)-aryl, OC(O)-styryl, substituted OC(O)-styryl; wherein the substituted glycoside is substituted by C(O)-aryl, substituted C(O)-aryl, C(O)-styryl, substituted C(O)-styryl; wherein said substituted aryl or substituted styryl may contain the substituents selected from the group consisting of halo, hydroxyl, nitro, cyano, amino, thiol, methylenedioxy, dihalomethylenedioxy, $C_1$–$C_6$ alkyl, $C_1$–$C_6$ alkoxy, $C_1$–$C_6$ haloalkyl, $C_1$–$C_6$-haloalkoxy, $C_3$–$C_8$ cycloalkyl, and $C_3$–$C_8$ cycloalkoxy;

bonding between adjacent monomers takes place at positions 4, 6 or 8;

X, Y and Z are selected from the group consisting of A and hydrogen, with the provisos that as to at least one terminal monomer, bonding of the adjacent monomer thereto is at position 4 and optionally Y=Z=hydrogen; and salts, derivatives and oxidation products thereof.

Preferably, the glycoside is selected from the group consisting of glucose, galactose, xylose, rhamnose and arabinose. Preferably, the —C(O)-aryl and —C(O)-styryl moieties are ester substituents derived from carboxylic acids selected from the group consisting of caffeic, cinnamic, coumaric, ferulic, gallic, hydroxybenzoic and sinapic acids. The glycoside or any or all of X, Y, and Z also can optionally be substituted at any position with substituted or unsubstituted —C(O)-aryl or —C(O)-styryl moieties via an ester bond.

These and other objects and embodiments are disclosed or will be obvious from the following Detailed Description.

SUMMARY OF THE INVENTION

Figure 1A:
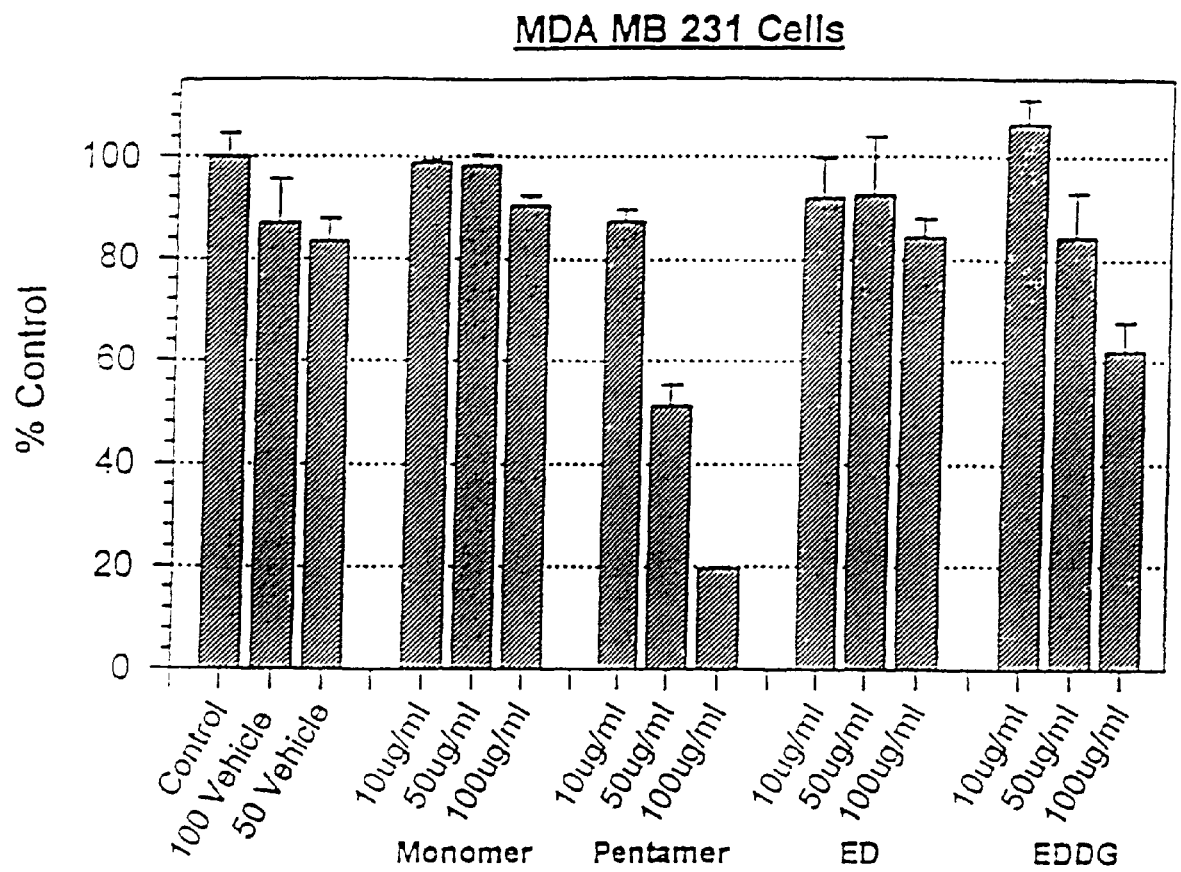
FIG. 1(a) is a bar graph showing the dose-response relationship between the control (solvent vehicle), monomer (epicatechin), pentamer (purified by preparative HPLC), ED (synthetic epicatechin dimer (EC-(4β→8)-EC)), and EDDG (synthesized epicatechin diner bisgallate (EC-3-O-galloyl-(4β→8)-EC-3-O-gallate) against the human breast cancer cell line MDA MB 231 at various μg/mL concentrations.

In one embodiment, the invention is directed to a process for the production of a polyphenol oligomer by coupling of protected polyphenol monomers, having protected phenolic hydroxyl groups, comprising the steps of:

(a) oxidizing the 4-position of a first protected polyphenol monomer to produce a first 4-alkoxy derivative polyphenol monomer;

(b) coupling said first 4-alkoxy derivative polyphenol monomer with a second protected polyphenol monomer to produce a protected polyphenol dimer;

(c) oxidizing the 4-position of a third protected polyphenol monomer to produce third 4-alkoxy derivative polyphenol monomer;

(d) coupling said third 4-alkoxy derivative polyphenol monomer with the protected polyphenol dimer to produce a protected polyphenol trimer;

(e) optionally repeating the oxidation and coupling steps to form a polyphenol oligomer comprised of n monomers, wherein n is an integer from 4 to 18. Advantageously, n is an integer from 5 to 12. The first, second and third polyphenol monomers may be the same or different.

In another embodiment, the invention is directed to a process for the production of a polyphenol oligomer, comprising:

(a) protecting each phenolic hydroxyl group of a first and a second polyphenol monomer with a protecting group to produce a protected polyphenol monomer;

(b) oxidizing the 4-position of the second protected polyphenol monomer to produce a 4-alkoxy derivative protected polyphenol monomer having the formula

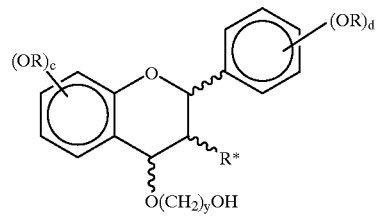

wherein c is an integer from 1 to 3;

d is an integer from 1 to 4;

y is an integer from 2 to 6;

R is a protecting group; and

R is H or OH;

(c) coupling the first protected polyphenol monomer with the 4-alkoxy derivative protected polyphenol monomer to produce the polyphenol oligomer, wherein said first and second polyphenol monomers are the same or different.

Advantageously, the functionalization and coupling steps are repeated to form a polyphenol oligomer wherein the polyphenol oligomer is comprised of n monomers, and n is an integer from 2 to 18. Preferably, n is an integer from 5–12.

The protecting group may be removed from the phenolic hydroxyl groups of the polyphenol oligomer to produce an unprotected polyphenol oligomer. In addition, the protected polyphenol oligomer may be esterified or glycosylated to produce a derivatized protected polyphenol oligomer. Alternatively, the unprotected polyphenol oligomer may be esterified or glycosylated to produce a derivatized polyphenol oligomer.

Preferably, the phenolic hydroxyl groups are protected with a benzyl protecting group, and y is 2.

In a further embodiment, the invention is directed to a process for the production of a polyphenol oligomer, which comprises:
(a) protecting each phenolic hydroxyl group of a (+)-catechin or of a (−)-epicatechin with a protecting group to produce a protected (+)-catechin or a protected (−)-epicatechin;
(b) oxidizing the 4-position of the protected (+)-catechin or of the protected (−)-epicatechin to produce a protected (+)-catechin 4-alkoxy derivative or a protected (−)-epicatechin 4-alkoxy derivative having the formula

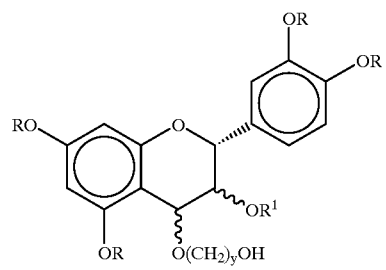

wherein
y is an integer from 2 to 6;
R is a protecting group; and
$R^1$ is hydrogen; and
(c) combining the protected (+)-catechin or the protected (−)-epicatechin with the functionalized protected (+)-catechin or the functionalized protected (−)-epicatechin to produce the polyphenol oligomer.

Advantageously, the protecting groups are removed from the phenolic hydroxyl groups of the polyphenol oligomer to produce an unprotected polyphenol oligomer. In addition, the protected polyphenol oligomer may be esterified or glycosylated to produce a derivatized protected polyphenol oligomer. Alternatively, the unprotected polyphenol oligomer may be esterified or glycosylated to produce a derivatized polyphenol oligomer.

Preferably, the phenolic hydroxyl groups are protected with a benzyl protecting group, and y is 2.

In other embodiments, the invention is directed to a process for the production of a derivatized polyphenol oligomer, which comprises esterifying a protected polyphenol oligomer, wherein each phenolic hydroxyl group of the polyphenol oligomer is protected, to produce an esterified polyphenol oligomer; to a process for the production of a derivatized polyphenol oligomer, which comprises glycosylating a protected polyphenol oligomer, wherein each phenolic hydroxyl group of the polyphenol oligomer is protected, to produce a glycosylated polyphenol oligomer; to a process for the production of a derivatized polyphenol oligomer, which comprises esterifying an unprotected polyphenol oligomer to produce an esterified polyphenol oligomer; and to a process for the production of a derivatized polyphenol oligomer, which comprises glycosylating an unprotected polyphenol oligomer to produce a glycosylated polyphenol oligomer.

In another embodiment, the invention is directed to a process of making a polyphenol oligomer comprised of n monomers of (+)-catechin or (−)-epicatechin, wherein n is an integer from 2 to 18, which comprises:
(a) protecting, with a protecting group, each phenolic hydroxyl group of a (+)-catechin or of a (−)-epicatechin to produce a protected (+)-catechin or a protected (−)-epicatechin;
(b) oxidizing the 4-position of the protected (+)-catechin or of the protected (−)-epicatechin to produce a protected (+)-catechin 4-alkoxy derivative or a protected (−)-epicatechin 4-alkoxy derivative having the formula

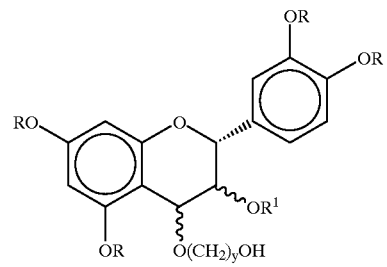

wherein
y is an integer from 2 to 6;
R is a protecting group; and
$R^1$ is hydrogen; and
(c) coupling the protected (+)-catechin or the protected (−)-epicatechin with the 4-alkoxy derivative protected (+)-catechin or the functionalized protected (−)-epicatechin to produce a protected polyphenol oligomer, wherein n equals 2; and
(d) removing the protecting group from each phenolic hydroxyl group of the protected polyphenol oligomer to produce the polyphenol oligomer, wherein n equals 2.

Advantageously, each phenolic hydroxyl group is protected using a benzyl ether protecting group, and y is 2.

The protected polyphenol oligomer, wherein n equals 2, may be coupled with the functionalized protected (+)-catechin or the functionalized protected (−)-epicatechin to produce a protected polyphenol oligomer, wherein n equals 3, followed by removal of the protecting group from each phenolic hydroxyl group of the protected polyphenol oligomer to produce the polyphenol oligomer, wherein n equals 3.

The process of coupling the protected polyphenol oligomer with the protected (+)-catechin 4-alkoxy derivative or the protected (−)-epicatechin 4-alkoxy derivative may be repeated to produce protected polyphenol oligomers, wherein n equals 4 to 18, followed by removal of the protecting group from each phenolic hydroxyl group of the protected polyphenol oligomer to produce the polyphenol oligomer, wherein n equals 4 to 18.

Derivatives of the dimers, trimers and higher oligomers may be formed from the protected polyphenol oligomer to produce a derivatized protected polyphenol oligomer, or from the unprotected polyphenol oligomer to produce a derivatized polyphenol oligomer.

In yet another embodiment, the invention is directed to a process for the production of a desired regio- or stereoisomer of a polyphenol oligomer of the formula

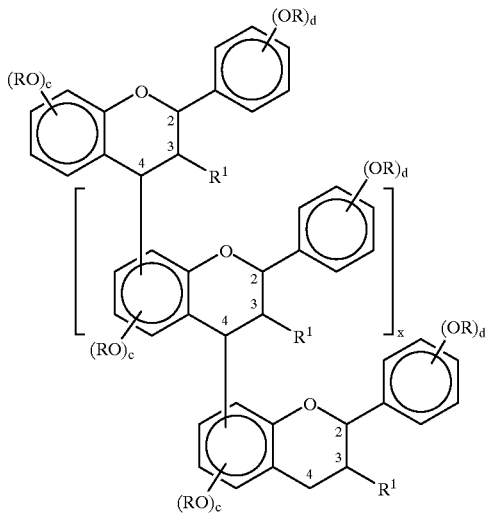

wherein
x is an integer from 0 to 16;
c is independently an integer from 1 to 3;
d is independently an integer from 1 to 4;
R is independently benzyl, substituted benzyl, and a silyl moiety containing $C_1$–$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$–$C_6$ alkyl, $C_1$–$C_6$ haloalkyl, $C_1$–$C_6$ alkoxy $C_1$–$C_6$ haloalkoxy, $C_3$–$C_8$ cycloalkyl, $C_3$–$C_8$ cycloalkoxy; and
$R^1$ is an O-glycoside, a substituted O-glycoside, OC(O)-aryl, substituted OC(O)-aryl, OC(O)-styryl, substituted OC(O)-styryl; wherein the substituted glycoside is substituted by C(O)-aryl, substituted C(O)-aryl, C(O)-styryl, substituted C(O)-styryl; wherein said substituted aryl or substituted styryl may contain the substituents selected from the group consisting of halo, hydroxyl, nitro, cyano, amino, thiol, methylenedioxy, dihalomethylenedioxy, $C_1$–$C_6$ alkyl, $C_1$–$C_6$ alkoxy, $C_1$–$C_6$ haloalkyl, $C_1$–$C_6$ haloalkoxy, $C_3$–$C_8$ cycloalkyl, and $C_3$–$C_8$ cycloalkoxy; and wherein each phenolic hydroxyl group of a polyphenol monomer is protected, comprising the steps of:
(a) oxidizing the 4-position of a first polyphenol monomer having a selected stereochemistry;
(b) coupling said 4-alkoxy derivative polyphenol monomer with a second polyphenol monomer having a selected stereochemistry to form a dimer having a selected regiochemistry;
(c) purifying said dimer;
(d) oxidizing the 4-position of a third polyphenol monomer having a selected stereochemistry;
(e) coupling said 4-alkoxy derivative third polyphenol monomer having a selected stereochemistry with said dimer to form a trimer having selected regiochemistry;
(f) purifying said trimer; and
(g) sequentially adding 4-alkoxy derivative polyphenol monomer to said trimer and successively higher oligomers by the steps recited above.

The invention is also directed to a process for producing a polyphenol oligomer of the formula

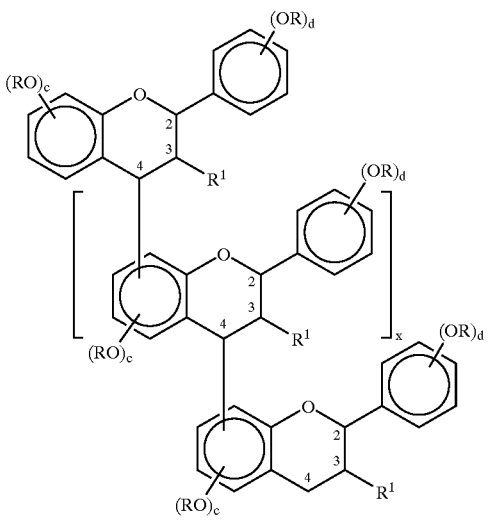

wherein
a bond to carbon position 2 has alpha or beta stereochemistry;
a bond to carbon position 3 has alpha or beta stereochemistry;
a bond to carbon position 4 has alpha or beta stereochemistry;
x is 0 to 16;
R is independently hydrogen, benzyl, substituted benzyl, and a silyl moiety containing $C_1$–$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$–$C_6$ alkyl, $C_1$–$C_6$ haloalkyl, $C_1$–$C_6$ alkoxy $C_1$–$C_6$ haloalkoxy, $C_3$–$C_8$ cycloalkyl, $C_3$–$C_8$ cycloalkoxy; and
$R^1$ is hydrogen, hydroxy, an O-glycoside, a substituted O-glycoside, OC(O)-aryl, substituted OC(O)-aryl, OC(O)-styryl, substituted OC(O)-styryl; wherein the substituted glycoside is substituted by C(O)-aryl, substituted C(O)-aryl, C(O)-styryl, substituted C(O)-styryl; wherein said substituted aryl or substituted styryl may contain the substituents selected from the group consisting of halo, hydroxyl, nitro, cyano, amino, thiol, methylenedioxy, dihalomethylenedioxy, $C_1$–$C_6$ alkyl, $C_1$–$C_6$ alkoxy, $C_1$–$C_6$ haloalkyl, $C_1$–$C_6$ haloalkoxy, $C_3$–$C_8$ cycloalkyl, and $C_3$–$C_8$ cycloalkoxy;
which comprises:
(a) reacting a compound of the formula

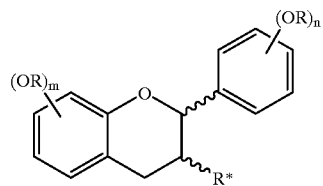

wherein
m is an integer from 1 to 3;

n is an integer from 1 to 4; and

R is benzyl, substituted benzyl, and a silyl moiety containing $C_1$–$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$–$C_6$ alkyl, $C_1$–$C_6$ haloalkyl, $C_1$–$C_6$ alkoxy $C_1$–$C_6$ haloalkoxy, $C_3$–$C_8$ cycloalkyl, $C_3$–$C_8$ cycloalkoxy; and R* is H or OH;

with a compound of the formula

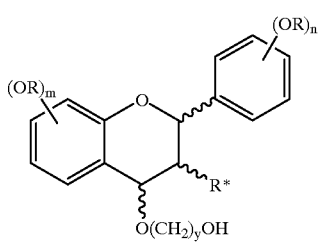

wherein m is an integer from 1 to 3;

n is an integer from 1 to 4;

y is an integer from 2 to 6; and

R is independently benzyl, substituted benzyl, and a silyl moiety containing $C_1$–$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$–$C_6$ alkyl, $C_1$–$C_6$ haloalkyl, $C_1$–$C_6$ alkoxy $C_1$–$C_6$ haloalkoxy, $C_3$–$C_8$ cycloalkyl, $C_3$–$C_8$ cycloalkoxy; and R* is H or OH;

to form a protected polyphenol oligomer having protected phenolic hydroxyl groups; and (b) deprotecting the phenolic hydroxyl groups of the protected polyphenol oligomer.

Advantageously, the polyphenol oligomer is derivatized, that is, $R^1$ is a glycoside, a substituted glycoside, C(O)-aryl, substituted C(O)-aryl, C(O)-styryl, substituted C(O)-styryl; wherein the substituted glycoside is substituted by C(O)-aryl, substituted C(O)-aryl, C(O)-styryl, substituted C(O)-styryl; wherein said substituted aryl or substituted styryl may contain the substituents selected from the group consisting of halo, hydroxyl, nitro, cyano, amino, methylenedioxy, substituted methylenedioxy, $C_1$–$C_6$ alkyl, $C_1$–$C_6$ alkoxy, $C_3$–$C_8$ cycloalkyl, and $C_3$–$C_8$ cycloalkoxy. Preferably, the glycoside is selected from the group consisting of glucose, galactose, xylose, rhamnose and arabinose. Alternatively, $R^1$ is derived from an acid selected from the group consisting of caffeic, cinnamic, coumaric, ferulic, gallic, hydroxybenzoic and sinapic acids.

In a further embodiment, the invention is directed to a process for producing a polyphenol oligomer of the formula

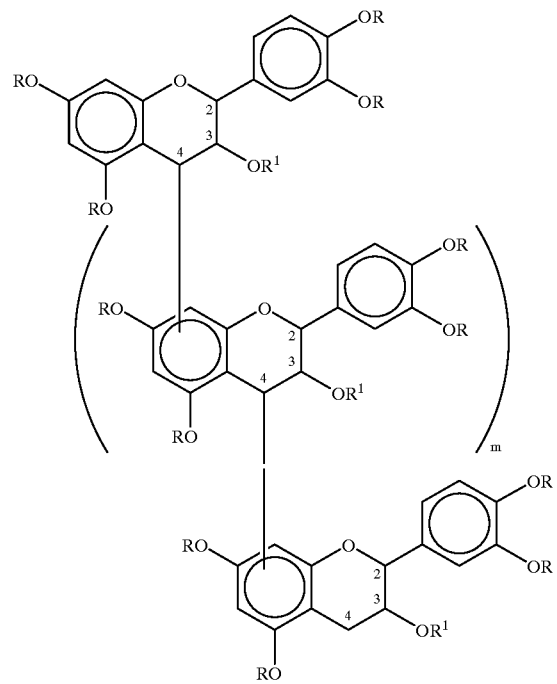

wherein a bond to carbon position 2 has alpha or beta stereochemistry;

a bond to carbon position 3 has alpha or beta stereochemistry;

a bond to carbon position 4 has alpha or beta stereochemistry;

m is 0 to 16;

R is hydrogen; and $R^1$ is hydrogen;

which comprises:

(a) reacting a compound selected from the group consisting of

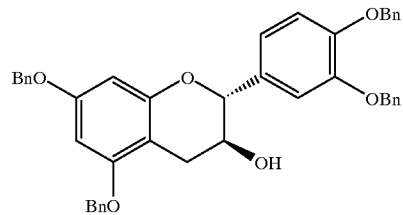

and

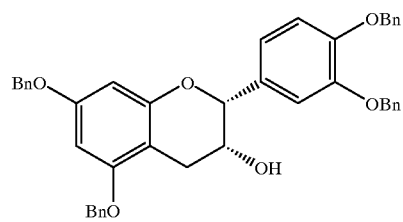

or a mixture thereof, with a compound selected from the group consisting of

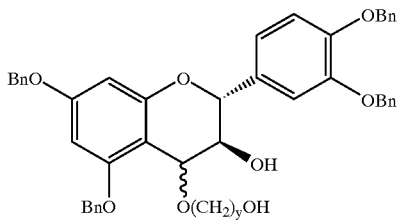

and

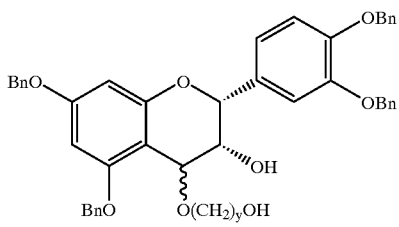

or a mixture thereof,
wherein
y is an integer from 2 to 6;
to form a protected polyphenol oligomer having benzylated phenolic hydroxyl groups; and
(b) deprotecting the benzylated phenolic hydroxyl groups of the protected polyphenol oligomer.

In a still further embodiment, the invention is directed to a process for producing a polyphenol oligomer of the formula

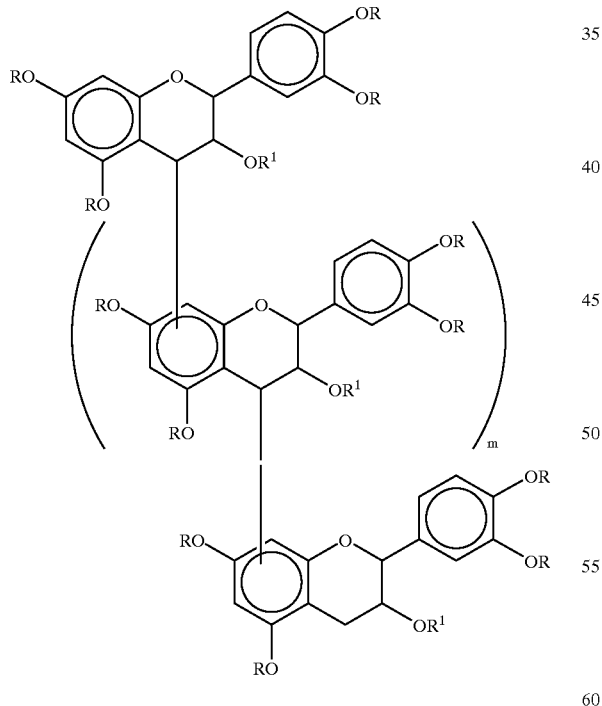

wherein
a bond to carbon position 2 has alpha or beta stereochemistry;
a bond to carbon position 3 has alpha or beta stereochemistry;
a bond to carbon position 4 has alpha or beta stereochemistry;

m is 1 to 16;
R is hydrogen; and
$R^1$ is hydrogen;
which comprises:
(a) reacting a compound of the formula

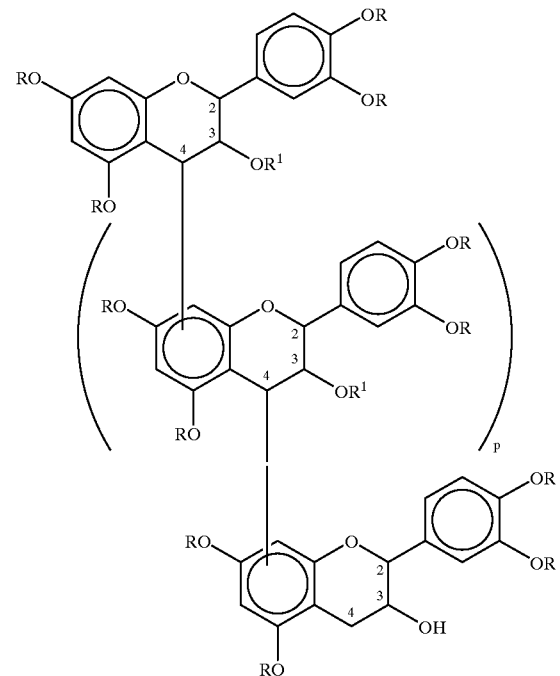

wherein
a bond to carbon position 2 has alpha or beta stereochemistry;
a bond to carbon position 3 has alpha or beta stereochemistry;
a bond to carbon position 4 has alpha or beta stereochemistry;
p is 0 to 15;
R is independently benzyl, substituted benzyl, and a silyl moiety containing $C_1$–$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$–$C_6$ alkyl, $C_1$–$C_6$ haloalkyl, $C_1$–$C_6$ alkoxy $C_1$–$C_6$ haloalkoxy, $C_3$–$C_8$ cycloalkyl, $C_3$–$C_8$ cycloalkoxy; and
$R^1$ is hydrogen, a glycoside, a substituted glycoside, C(O)-aryl, substituted C(O)-aryl, C(O)-styryl, substituted C(O)-styryl; wherein the substituted glycoside is substituted by C(O)-aryl, substituted C(O)-aryl, C(O)-styryl, substituted C(O)-styryl; wherein said substituted aryl or substituted styryl may contain the substituents selected from the group consisting of halo, hydroxyl, nitro, cyano, amino, thiol, methylenedioxy, dihalomethylenedioxy, $C_1$–$C_6$ alkyl, $C_1$–$C_6$ alkoxy, $C_1$–$C_6$ haloalkyl, $C_1$–$C_6$ haloalkoxy, $C_3$–$C_8$ cycloalkyl, and $C_3$–$C_8$ cycloalkoxy; with a compound selected from the group consisting of

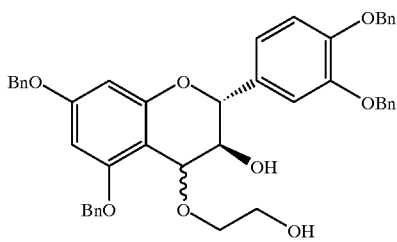

and

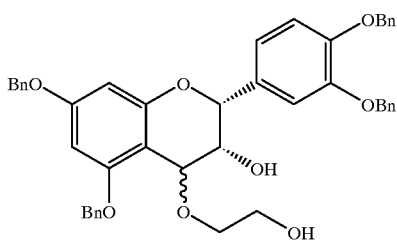

or a mixture thereof,
wherein
m=p+1.

In another embodiment, the invention is directed to a process for the production of a polyphenol oligomer, comprising:

(a) protecting each phenolic hydroxyl group of a first and a second polyphenol monomer using a protecting group to produce a first and a second protected polyphenol monomer;

(b) oxidizing the 4-position of the second protected polyphenol monomer using a quinone oxidizing agent in the presence of a diol to provide a protected 4-alkoxy polyphenol derivative having the formula:

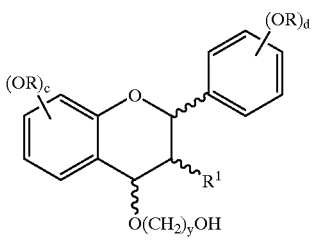

wherein
c is an integer from 1 to 3;
d is an integer from 1 to 4;
y is an integer from 2 to 6;
R is a protecting group; and
$R^1$ is H or OH;

(c) coupling the first protected polyphenol monomer and the 4-alkoxy derivative polyphenol monomer using an acid catalyst to provide a protected polyphenol oligomer; and (d) deprotecting the protected polyphenol oligomer to provide the polyphenol oligomers, wherein the first and second polyphenol monomers are the same or different.

In yet another embodiment, the invention is directed to a process for the production of a polyphenol oligomer by coupling of polyphenol monomers, wherein each phenolic hydroxyl group of the polyphenol monomer is protected, comprising the steps of:

(a) oxidizing the 4-position of a first protected polyphenol monomer to produce 4-alkoxy derivative polyphenol monomer;

(b) substituting the 6- or 8-position of a protected polyphenol, wherein the polyphenol is a protected monomer or a protected oligomer, to produce a blocked polyphenol; and (b) coupling said 4-alkoxy derivative polyphenol monomer with said blocked polyphenol to form the polyphenol oligomer.

Advantageously, the 8-position of the blocked polyphenol is substituted such that the 4-position of the 4-alkoxy derivative polyphenol monomer is coupled to the 6-position of the blocked polyphenol.

The invention is also directed to a process for the production of a desired regio- or stereoisomer of a polymeric compound of the formula $A_n$, wherein A is a monomer of the formula:

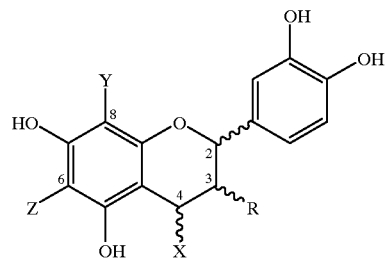

wherein
n is an integer from 3 to 18, such that there is at least one terminal monomeric unit A, and a plurality of additional monomeric units;

R is 3-($\alpha$)-OH, 3-($\beta$)-OH, 3-($\alpha$)-O-sugar, or 3-($\beta$)-O-sugar;

bonding between adjacent monomers takes place at positions selected from the group consisting of 4, 6 and 8;

a bond for an additional monomeric unit in position 4 has alpha or beta stereochemistry;

X, Y and Z are selected from the group consisting of monomeric unit A, hydrogen, and a sugar, with the provisos that as to the at least one terminal monomeric unit, bonding of the additional monomeric unit thereto is at position 4 and optionally Y=Z=hydrogen;

the sugar is optionally substituted with a phenolic moiety, and pharmaceutically acceptable salts, derivatives thereof, and oxidation products thereof;

which process comprises the steps of:

(a) oxidizing the 4-position of a first polyphenol monomer;

(b) reacting said 4-alkoxy derivative polyphenol monomer with a second polyphenol monomer to form a dimer;

(c) purifying said dimer;

(d) oxidizing the 4-position of a third polyphenol monomer;

(e) reacting said 4-alkoxy derivative third polyphenol monomer with said dimer to form a trimer;

(f) purifying said trimer;

(g) sequentially adding 4-alkoxy derivative polyphenol monomer to said trimer and successively higher oligomers by the steps recited above; and (h) optionally derivatizing the protected or unprotected polyphenol oligomer to produce a esterify or glycoslylate polyphenol oligomer. Advantageously, n is 5, the sugar is selected from the group consisting of glucose, galactose, xylose, rhamnose and arabinose, and the phenolic moiety is selected from the group consisting of caffeic, cinnamic, coumaric, ferulic, gallic, hydroxybenzoic and sinapic acids.

The invention is further directed to a process for the production of a polymeric compound of the formula $A_n$, wherein A is a monomer of the formula:

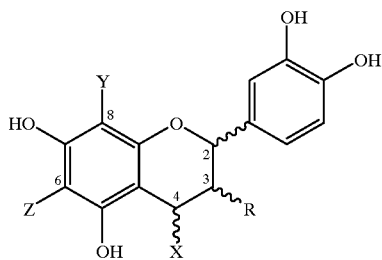

wherein n is an integer from 3 to 18, such that there is at least one terminal monomeric unit A, and a plurality of additional monomeric units;

R is 3-($\alpha$)-OH, 3-($\beta$)-OH, 3-($\alpha$)-O-sugar, or 3-($\beta$)-O-sugar;

bonding between adjacent monomers takes place at positions selected from the group consisting of 4, 6 and 8;

a bond for an additional monomeric unit in position 4 has alpha or beta stereochemistry;

X, Y and Z are selected from the group consisting of monomeric unit A, hydrogen, and a sugar, with the provisos that as to the at least one terminal monomeric unit, bonding of the additional monomeric unit thereto is at position 4 and optionally Y=Z=hydrogen;

the sugar is optionally substituted with a phenolic moiety, and pharmaceutically acceptable salts, derivatives thereof, and oxidation products thereof;

which process comprises:
(a) protecting each phenolic hydroxyl group of a (+)-catechin or of a (−)-epicatechin with a protecting group to produce a protected (+)-catechin or a protected (−)-epicatechin;
(b) oxidizing the 4-position of the protected (+)-catechin or of the protected (−)-epicatechin or of a mixture thereof to produce a protected (+)-catechin 4-alkoxy derivative, a protected (−)-epicatechin 4-alkoxy derivative or a mixture thereof;
(c) combining the protected (+)-catechin or the protected (−)-epicatechin with the protected (+)-catechin 4-alkoxy derivative or the protected (−)-epicatechin 4-alkoxy derivative or mixtures thereof to produce a protected polyphenol oligomer;
(d) removing the protecting group from the phenolic hydroxyl groups of the polyphenol oligomer to produce an unprotected polyphenol oligomer; and
(e) optionally esterifying or glycosylating the protected or unprotected polyphenol oligomer to produce a derivatized polyphenol oligomer.

In still another embodiment, the invention is directed to a polymeric compound of the formula $A_n$, wherein A is a monomer of the formula:

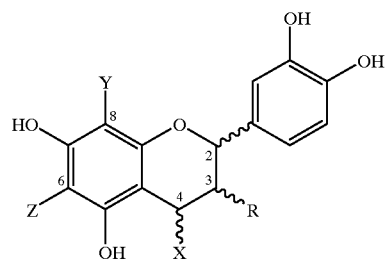

wherein n is an integer from 3 to 18, such that there is at least one terminal monomeric unit A, and a plurality of additional monomeric units;

R is 3-($\alpha$)-OH, 3-($\beta$)-OH, 3-($\alpha$)-O-sugar, or 3-($\beta$)-O-sugar;

bonding between adjacent monomers takes place at positions selected from the group consisting of 4, 6 and 8;

a bond for an additional monomeric unit in position 4 has alpha or beta stereochemistry;

X, Y and Z are selected from the group consisting of monomeric unit A, hydrogen, and a sugar, with the provisos that as to the at least one terminal monomeric unit, bonding of the additional monomeric unit thereto is at position 4 and optionally Y=Z=hydrogen;

the sugar is optionally substituted with a phenolic moiety, and pharmaceutically acceptable salts, derivatives thereof, and oxidation products thereof.

Advantageously, n is 5, the sugar is selected from the group consisting of glucose, galactose, xylose, rhamnose and arabinose, and the phenolic moiety is selected from the group consisting of caffeic, cinnamic, coumaric, ferulic, gallic, hydroxybenzoic and sinapic acids.

Also advantageously, the compound is substantially pure, preferably purified to apparent homogeneity.

Derivatives of the compound wherein one or more of the phenolic hydroxyl groups is benzylated are also encompassed within the scope of the invention.

Adjacent monomers may bind at position 4 by (4→6) or (4→8); and each of X, Y and Z is H, a sugar or an adjacent monomer, with the provisos that if X and Y are adjacent monomers, Z is H or sugar and if X and Z are adjacent monomers, Y is H or sugar, and that as to at least one of the two terminal monomers, bonding of the adjacent monomer is at position 4 and optionally, Y=Z=hydrogen.

One or more of the monomeric units may be derivatized with a gallate or a $\beta$-D-glucose, including the 3-position of a terminal monomeric unit.

In still yet another embodiment, the invention is directed to a pharmaceutical composition comprising a compound of the formula

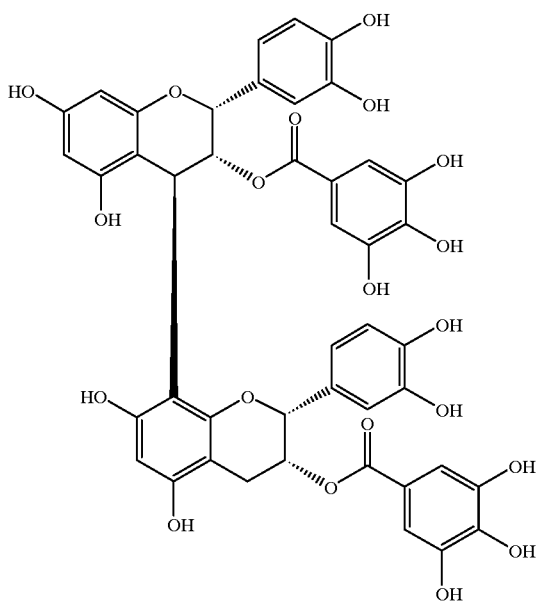

and a pharmaceutically acceptable carrier or excipient, and to a method for treating a subject in need of treatment with an anticancer agent comprising administering to the subject an effective amount of the composition. The cancer includes breast cancer.

In still yet another embodiment, the invention is directed to a pharmaceutical composition comprising a compound of the formula

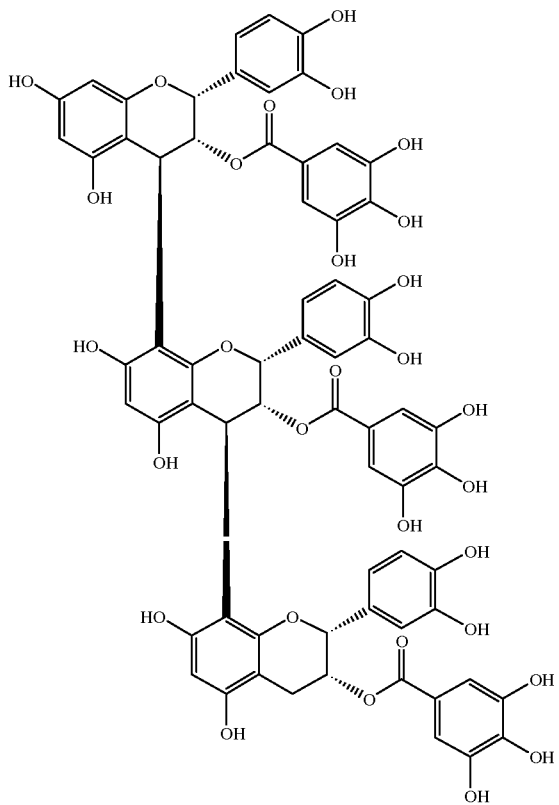

and a pharmaceutically acceptable carrier or excipient, and to a method for treating a subject in need of treatment with an anticancer agent comprising administering to the subject an effective amount of the composition. The cancer includes breast cancer.

The invention is also directed to a compound of the formula

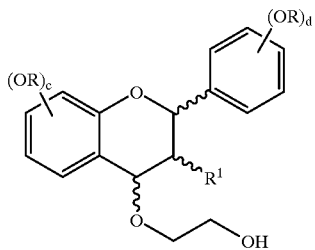

wherein
  c is an integer from 1 to 3;
  d is an integer from 1 to 4;
  R is benzyl, substituted benzyl, and a silyl moiety containing $C_1$–$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$–$C_6$ alkyl, $C_1$–$C_6$ haloalkyl, $C_1$–$C_6$ alkoxy $C_1$–$C_6$ haloalkoxy, $C_3$–$C_8$ cycloalkyl, $C_3$–$C_8$ cycloalkoxy; and
  $R^1$ is hydrogen, hydroxy, an O-glycoside, a substituted O-glycoside, OC(O)-aryl, substituted OC(O)-aryl, OC(O)-styryl, substituted OC(O)-styryl; wherein the substituted glycoside is substituted by C(O)-aryl, substituted C(O)-aryl, C(O)-styryl, substituted C(O)-styryl; wherein said substituted aryl or substituted styryl may contain the substituents selected from the group consisting of halo, hydroxyl, nitro, cyano, amino, thiol, methylenedioxy, dihalomethylenedioxy, $C_1$–$C_6$ alkyl, $C_1$–$C_6$ alkoxy, $C_1$–$C_6$ haloalkyl, $C_1$–$C_6$ haloalkoxy, $C_3$–$C_8$ cycloalkyl, and $C_3$–$C_8$ cycloalkoxy.

DETAILED DESCRIPTION OF THE INVENTION

The present invention relates to a method of synthesizing polyphenol oligomers and derivatives thereof. The subject compounds of the invention have the same uses, and are formulated, purified and administered in the same manner as described in U.S. application Ser. No. 08/831,245 filed Apr. 2, 1997.

As used herein, the term polyphenols means a flavan compound having the formula

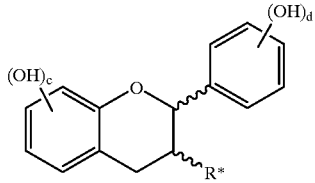

wherein
  c is an integer from 1 to 3;
  d is an integer from 1 to 4;
  R* is H or OH;
and derivatives thereof.

The term polyphenols includes proanthocyanidins, and derivatives thereof, as well as structurally similar synthetic materials, and specifically includes procyanidins, such as those that can be extracted from cocoa beans, and derivatives thereof, as well as structurally similar synthetic materials.

Representative proanthocyanidins include:

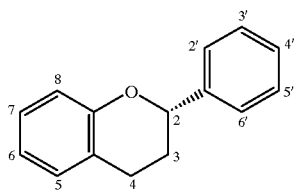

| Class | Monomer | Substitution Pattern | | | | | | |
|---|---|---|---|---|---|---|---|---|
| | | 3 | 5 | 7 | 8 | 3' | 4' | 5' |
| Proapigeninidin | Apigeniflavan | H | OH | OH | H | H | OH | H |
| Proluteolinidin | Luteoliflavan | H | OH | OH | H | OH | OH | H |
| Protricetinidin | Tricetiflavan | H | OH | OH | H | OH | OH | OH |
| Propelargonidin | Afzelechin | OH | OH | OH | H | H | OH | H |
| Procyanidin | Catechin | OH | OH | OH | H | OH | OH | H |
| Prodelphinidin | Gallocatechin | OH | OH | OH | H | OH | OH | OH |
| Proguibourtinidin | Guibourtinidol | OH | H | OH | H | H | OH | H |
| Profisetinidin | Fisetinidol | OH | H | OH | H | OH | OH | H |
| Prorobinetinidin | Robinetinidol | OH | H | OH | H | OH | OH | OH |
| Proteracacinidin | Oritin | OH | H | OH | OH | H | OH | H |
| Promelacacinidin | Prosopin | OH | H | OH | OH | OH | OH | H |

The present invention provides a method of preparing substantially pure polyphenol oligomers, and derivatives thereof.

In a preferred embodiment, the present invention provides a process of synthesizing polyphenol oligomers of the formula:

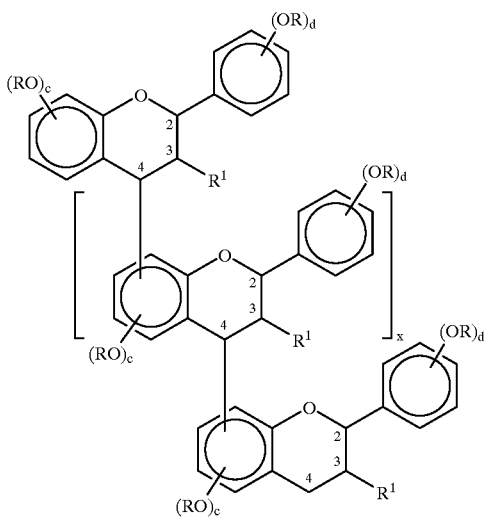

or

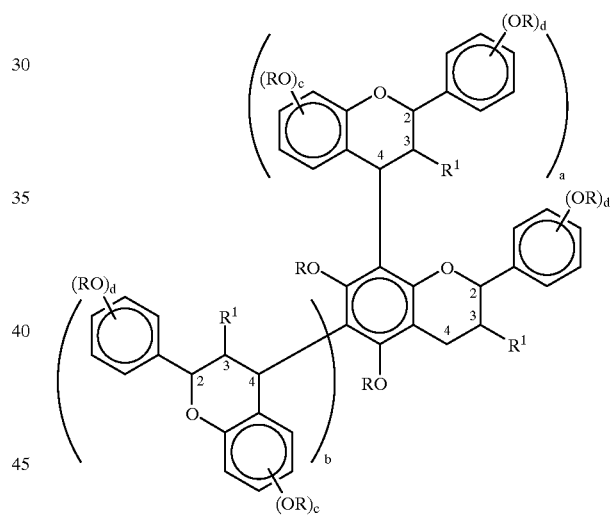

wherein
x is an integer from 0 to 16;
a is an integer from 1 to 15;
b is an integer from 1 to 15;
the sum a+b is an integer from 2 to 17;
c is independently an integer from 1 to 3;
d is independently an integer from 1 to 4;

R is independently hydrogen, benzyl, substituted benzyl, and a silyl moiety containing $C_1$–$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$–$C_6$ alkyl, $C_1$–$C_6$ haloalkyl, $C_1$–$C_6$ alkoxy $C_1$–$C_6$ haloalkoxy, $C_3$–$C_8$ cycloalkyl, $C_3$–$C_8$ cycloalkoxy; and $R^1$ is hydrogen, hydroxy, an O-glycoside, a substituted O-glycoside, OC(O)-aryl, substituted OC(O)-aryl, OC(O)-styryl, substituted OC(O)-styryl; wherein the substituted glycoside is substituted by C(O)-aryl, substituted C(O)-aryl, C(O)-styryl, substituted C(O)-styryl; wherein said substituted aryl or substituted styryl may contain the substituents selected from the group consisting of halo, hydroxyl, nitro, cyano, aryl, amino, methylenedioxy, dihalomethylenedioxy, $C_1$–$C_6$ alkyl, $C_1$–$C_6$ alkoxy, $C_1$–$C_6$ haloalkyl, $C_1$–$C_6$ haloalkoxy, $C_3$–$C_8$ cycloalkyl, and $C_3$–$C_8$ cycloalkoxy; and wherein said process comprises the steps of:

(i) subjecting a first polyphenol monomer to conditions sufficient to produce a C-4 functionalized intermediate; and (ii) coupling the C-4 functionalized intermediate with a second polyphenol monomer or an oligomer having up to 17 repeat units that are the same or different. The first and second polyphenol monomers may be the same or different.

Specifically, the present invention provides a method of preparing substantially pure cocoa polyphenol oligomers, and derivatives thereof. The oligomeric compounds are comprised of n polyphenol monomeric units, wherein n is an integer of 2 through 18, preferably 2 through 5, or 4 through 12, more preferably n is 3 through 12, and most preferably n is 5 through 12, and having linkages of 4→6 and 4→8.

The term "oligomer", as used herein, refers to any compound of the formula presented above, wherein x is 0 through 16, and higher. When x is 0, the oligomer is termed a "dimer"; when x is 1, the oligomer is termed a "trimer"; when x is 2, the oligomer is termed a "tetramer"; when x is 3, the oligomer is termed a "pentamer"; and similar recitations may be designated for oligomers having x up to and including 16 and higher, such that when x is 16, the oligomer is termed an "octadecamer".

The inventive compounds can be purified, e.g., compounds or combinations thereof can be substantially pure; for instance, purified to apparent homogeneity. Purity is a relative concept, and the numerous Examples demonstrate isolation of inventive compounds or combinations thereof, as well as purification thereof, such that by methods exemplified a skilled artisan can obtain a substantially pure inventive compound or combination thereof, or purify them to apparent homogeneity (e.g., purity by HPLC: observation of a single chromatographic peak). As defined herein, a substantially pure compound or combination of compounds is at least about 40% pure, e.g., at least about 50% pure, advantageously at least about 60% pure, e.g., at least about 70% pure, more advantageously at least about 75–80% pure, preferably, at least about 90% pure, more preferably greater than 90% pure, e.g., at least 90–95% pure, or even purer, such as greater than 95% pure, e.g., 95–98% pure.

Linear and branched polyphenol oligomers may be prepared by the method of the present invention. Any polyphenol, as exemplified above, may be used to prepare linear or branched oligomers containing repeating monomeric units of the same polyphenol or of different polyphenols. The possible linkages between monomers comprising the oligomers are distinguished by Top (T), Middle (M), Junction (J), and Bottom (B) linkages. Representative examples for a linear pentamer and branched pentamer are shown below.

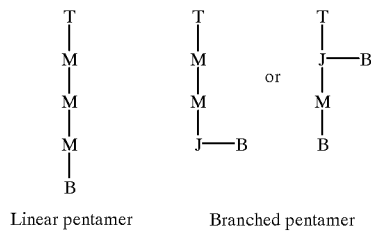

Linear pentamer    Branched pentamer

Further regioisomers of the polyphenol oligomers are encompassed within the scope of this invention.

Polyphenols, (+)-catechin and (−)-epicatechin, are used herein to exemplify the types of polyphenol oligomers that may be prepared by the method of the present invention. The linkages between adjacent the polyphenol monomers, (+)-catechin and (−)-epicatechin, abbreviated C and EC, respectively, are from position 4 to position 6 or position 4 to position 8; and this linkage between position 4 of a monomer and position 6 and 8 of the adjacent monomeric units is designated herein as (4→6) or (4→8).

Moreover, stereoisomers of the oligomers are encompassed within the scope of the invention. The stereochemistry of the substituents on a flavonoid monomer of the oligomer may be described in terms of their relative stereochemistry, "alpha/beta" or "cis/trans", or in terms of absolute stereochemistry, "R/S". The term "alpha" (α) indicates that the substituent is oriented below the plane of the flavan ring, whereas, "beta" (β) indicates that the substituent is oriented above the plane of the ring. The term "cis" indicates that two substituents are oriented on the same face of the ring, whereas "trans" indicates that two substituents are oriented on opposite faces of the ring. The terms R and S are used to denote the arrangement of the substituents about a stereogenic center, based on the ranking of the groups according to the atomic number of the atoms directly attached to that stereogenic center. For example, the polyphenol, (+)-catechin, may be defined as (2R,trans)-2-(3',4'-dihydroxyphenyl)-3,4-dihydro-2H-1-benzopyran-3,5,7-triol, or as (2R, 3S)-flavan-3,3',4',5,7-pentaol. Interflavan (polyphenol-polyphenol) bonding is often characterized using the relative terms α/β or cis/trans; α/β is used herein to designate the relative stereochemistry of the interflavan bonding.

There are multiple stereochemical linkages between position 4 of a monomer and position 6 and 8 of the adjacent monomer; and the stereochemical linkages between monomeric units is designated herein as (4α→6) or (4β→6) or (4α→8) or (4β→8) for linear oligomers. For linkages to a branched or junction monomer, the stereochemical linkages are (6→4α) or (6→4β) or (8→4α) or (8→4β). When C is linked to another C or EC, the linkages are advantageously (4α→6) or (4α→8). When EC is linked to C or another EC, the linkages are advantageously (4β→6) or (4β→8).

In addition to carbon position 4, a bond to carbon position 2 has alpha or beta stereochemistry, and a bond to carbon position 3 has alpha or beta stereochemistry (e.g., (−)-epicatechin or (+)-catechin).

Examples of compounds within the scope of this invention include dimers, EC-(4β→8)-EC and EC-(4β→6)-EC, wherein EC-(4β→8)-EC is preferred; trimers

[EC-(4β→8)]$_2$-EC, [EC-(4β→8)]$_2$-C and [EC-(4β→6)]$_2$-EC, wherein [EC-(4β→8)]$_2$-EC is preferred; tetramers [EC-(4β→8)]$_3$-EC, [EC-(4β→8)]$_3$-C and [EC-(4β→8)]$_2$-EC-(4β→6)-C, wherein [EC-(4β→8)]$_3$-EC is preferred; and pentamers [EC-(4β→8)]$_4$-EC, [EC-(4β→8)]$_3$-EC-(4β→6)-EC, [EC-(4β→8)]$_3$-EC-(4β→8)-C and [EC-(4β→8)]$_3$-EC-(4β→6)-C, wherein [EC-(4β→8)]$_4$-EC is preferred. An example of a branched trimer is

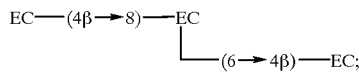

examples of a branched tetramer include

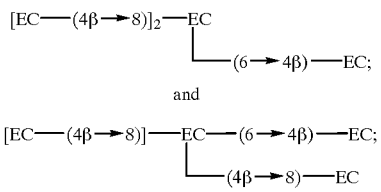

an example of a branched pentamer is

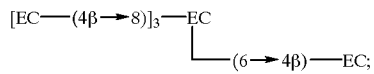

Additionally, compounds which elicit the activities cited above also include hexamers to dodecamers, examples of which are listed below:

A hexamer, wherein one monomer (C or EC) is linked to a pentamer compound listed above, e.g., [EC-(4β→8)]$_5$-EC, [EC-(4β→8)]$_4$-EC-(4β→6)-EC, [EC-(4β→8)]$_4$-EC-(4β→8)-C, and [EC-(4β→8)]4-EC-(4β→6)-C; wherein [EC-(4β→8)]$_5$-EC is preferred; an example of a branched hexamer is

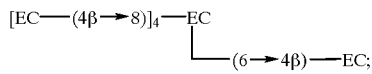

A heptamer, wherein any combination of two monomers (C and/or EC) is linked to a pentamer compound listed above, e.g., [EC-(4β→8)]$_6$-EC, [EC-(4β→8)]$_5$-EC-(4β→6)-EC, [EC-(4β→8)]$_5$-EC-(4β→8)-C, and [EC-(4β→8)]$_5$-EC-(4β→6)-C; in a preferred embodiment, the heptamer is [EC-(4β→8)]$_6$-EC; an example of a branched heptamer is

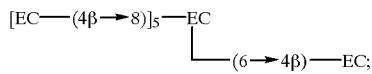

An octamer, wherein any combination of three monomers (C and/or EC) is linked to a pentamer compound listed above, e.g., [EC-(4β→8)]$_7$-EC, [EC-(4β→8)]$_6$-EC-(4β→6)-EC, [EC-(4β→8)]$_6$-EC-(4β→8)-C, and [EC-(4β→8)]$_6$-EC-(4β→6)-C; in a preferred embodiment, the octamer is [EC-(4β→8)]$_7$-EC; an example of a branched octamer is

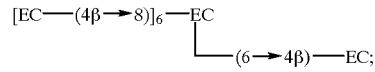

A nonamer, wherein any combination of four monomers (C and/or EC) is linked to a pentamer compound listed above, e.g., [EC-(4β→8)]$_8$-EC, [EC-(4β→8)]$_7$-EC-(4β→6)-EC, [EC-(4β→8)]$_7$-EC-(4β→8)-C, and [EC-(4β→8)]$_7$-EC-(4β→6)-C; in a preferred embodiment, the nonamer is [EC-(4β→8)]$_8$-EC; an example of a branched nonamer is

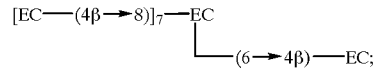

A decamer, wherein any combination of five monomers (C and/or EC) is linked to a pentamer compound listed above, e.g., [EC-(4β→8)]$_9$-EC, [EC-(4β→8)]-EC-(4β→6)-EC, [EC-(4β→8)]$_8$-EC-(4β→8)-C, and [EC-(4β→8)]$_8$-EC-(4β→6)-C; in a preferred embodiment, the decamer is [EC-(4β→8)]$_9$-EC; an example of a branched decamer is

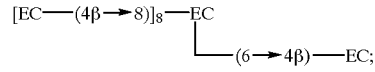

An undecamer, wherein any combination of six monomers (C and/or EC) is linked to a pentamer compound listed above, e.g., [EC-(4β→8)]$_{10}$-EC, [EC-(4β→8)]$_9$-EC-(4β→6)-EC, [EC-(4β→8)]$_9$-EC-(4β→8)-C, and [EC-(4β→8)]$_9$-EC-(4β→6)-C; in a preferred embodiment, the undecamer is [EC-(4β→8)]$_{10}$-EC; an example of a branched undecamer is

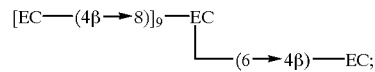

A dodecamer, wherein any combination of seven monomers (C and/or EC) is linked to a pentamer compound listed above, e.g., [EC-(4β→)]$_{11}$-EC, [EC-(4β→8)]$_{10}$-EC-(4β→6)-EC, [EC-(4β→8)]$_{10}$-EC-(4β→8)-C, and [EC-(4β→8)]$_{10}$-EC-(4β→6)-C; in a preferred embodiment, the dodecamer is [EC-(4β→8)]$_{11}$-EC; an example of a branched dodecamer is

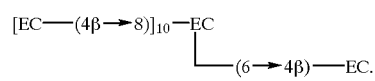

It will be understood from the detailed description that the aforementioned list is exemplary and is provided to illustrate the types of compounds that may be prepared by the methods of the present invention and is not intended as an exhaustive list of the inventive compounds encompassed by the present invention.

One skilled in the art will appreciate that rotation of a number of bonds within the oligomer may be restricted due to steric hindrance, particularly if the oligomer is substituted, such as with benzyl groups.

Accordingly, all possible regioisomers and stereoisomers of the compounds of the invention are encompassed within the scope of the invention.

Linear and branched polyphenol oligomers may be prepared by the method of the present invention using a sequence comprising protection, functionalization, coupling and deprotection reactions. In each reaction sequence, any polyphenol, as exemplified above, may be used to prepare linear or branched oligomers containing repeating monomeric units of the same polyphenol or of different polyphenols. Higher oligomers may be prepared by repeating the coupling step by coupling a dimer, trimer, or higher oligomer with additional monomer.

The method of the present invention comprises:

(a) protecting each phenolic hydroxyl group of a first and second polyphenol monomer using a suitable phenol protecting group to provide a first and a second protected polyphenol monomer (wherein the first and second polyphenols may be the same or different);

(b) oxidizing the 4-position of a second protected polyphenol monomer using an oxidizing agent to provide a protected 4-alkoxy polyphenol derivative;

(c) coupling the first protected polyphenol and the oxidized polyphenol monomer using a catalyst to provide a polyphenol oligomer; and (d) deprotecting the polyphenol oligomer to provide unprotected polyphenol oligomers.

Exemplary oxidizing agents useful in the method of the invention include quinone-type oxidizing agents and metal acetate oxidizing agents (e.g. lead tetraacetate).

Preferably, the method of the present invention comprises:

(a) protecting each phenolic hydroxyl group of a first and a second polyphenol monomer using a benzyl ether protecting group to produce a first and a second protected polyphenol monomer;

(b) oxidizing the 4-position of the second protected polyphenol monomer using a quinone oxidizing agent in the presence of an alcohol, preferably a diol, to provide a 4-alkoxy functionalized protected polyphenol having the formula;

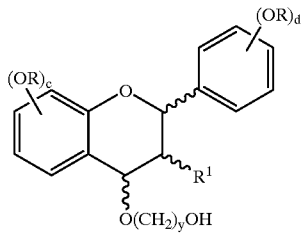

wherein
c is an integer from 1 to 3;
d is an integer from 1 to 4;
y is an integer from 2 to 6;
R is a protecting group; and
$R^1$ is H or OH;

(c) coupling the first protected polyphenol monomer and the oxidized polyphenol monomer using a protic acid catalyst or a Lewis Acid catalyst to provide a polyphenol oligomer, the coupled polyphenol monomers being the same or different; and (d) deprotecting the polyphenol oligomer to provide unprotected polyphenol oligomers.

Hydrochloric acid (HCl) is an exemplary protic acid catalyst useful in the method of the present invention. A particularly useful form of hydrochloric acid is an anhydrous solution in dioxane. Exemplary Lewis Acid catalysts that are useful in the present invention include titanium tetrahalides (e.g. titanium tetrachloride), aluminum trihalides (e.g. aluminum trichloride), boron trihalides (e.g. boron trifluoride etherate), trialkyl or triaryl silyl compounds (e.g. trimethyl silyl triflate) and the like.

More preferably, the method of the present invention comprises:

(a) protecting each phenolic hydroxyl group of a first and a second polyphenol monomer using a benzyl ether protecting group to produce a first and a second protected polyphenol monomer;

(b) oxidizing the 4-position of the second protected polyphenol monomer using 2,3-dichloro-5,6-dicyano-1,4-benzoquinone in the presence of ethylene glycol to provide a protected 4-alkoxy polyphenol derivative having the formula

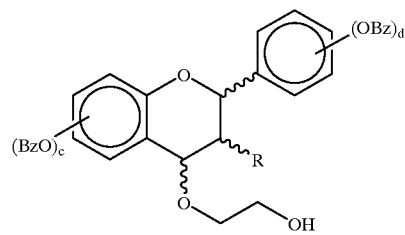

wherein
R=H or OH;
c is an integer from 1 to 3;
d is an integer from 1 to 4; and
Bz represents a benzyl moiety (c) coupling the first protected polyphenol monomer and the second oxidized polyphenol monomer using titanium tetrachloride to provide a polyphenol oligomer, the coupled polyphenol monomers being the same or different; and (d) deprotecting the polyphenol oligomer to provide unprotected polyphenol oligomers.

An important transformation in the reaction sequence of the present invention is the formation of the protected 4-alkoxy polyphenol intermediate used in the oligomer-forming coupling reaction. It has been determined that high purity of this intermediate is important for obtaining oligomeric products in good purity. Advantageously, it has been discovered that formation of the 4-alkoxy polyphenol using ethylene glycol, in place of lower alkyl alcohols, provides a 4-alkoxy polyphenol derivative that may be readily purified by chromatography. Use of methanol, ethanol, or even isopropyl alcohol, provides 4-alkoxy polyphenols that are not separable or difficult to separate chromatographically from the non-oxidized phenol and from byproducts and cannot be used satisfactorily in the oligomer-forming coupling reaction. Accordingly, another aspect of the present invention comprises providing a pure 4(2-hydroxyethyl) 4-alkoxy polyphenol intermediate useful for forming polyphenol oligomers.

The skilled artisan will recognize that the reaction sequence discussed above may be modified at the final stages to yield oligomers having x=2–16, without undue experimentation. Higher oligomers, i.e., x=2–16, can be isolated by employing the dimer and/or trimer as the starting material for the coupling reaction, and the products derived therefrom may subsequently be used as starting material for coupling reactions to produce even higher oligomers.

Moreover, the skilled artisan will recognize that various reagents can be employed to practice the inventive method, without undue experimentation, and without departing from the spirit or scope thereof. Skilled artisans will be able to envision additional routes of synthesis, based on this disclosure and the knowledge in the art, without undue experimentation, e.g, based upon a careful retrosynthetic analysis of the polymeric compounds, as well as the monomers. For example, coupling of polyphenols via an organometallic intermediate has been reported by K. Weinges et al. *Chem. Ber.* 103, 2344–2349 (1970). In addition, linear and branched polyphenol oligomers may be prepared by direct acid catalyzed coupling of monomeric polyphenol units, using conditions described by L. Y. Foo and R. W. Hemingway, *J. Chem. Soc., Chem. Commun.*, 85–86 (1984); J. J. Botha, et al., *J. Chem. Soc., Perkin I,* 1235–1245 (1981); J. J. Botha et al.; *J. Chem. Soc., Perkin I,* 527–533 (1982), and H. Kolodziej, *Phytochemistry* 25, 1209–1215 (1986).

These methods may be used to prepare linear or branched oligomers containing repeating monomeric units of a single polyphenol or of different polyphenols. Moreover, given the phenolic character of the subject compounds, the skilled artisan can utilize various methods of phenolic coupling, selective protection/deprotection, organometallic additions, and photochemical reactions, e.g., in a convergent, linear or biomimetic approach, or combinations thereof, together with standard reactions known to those well-versed in the art of synthetic organic chemistry, as additional synthetic methods for preparing polyphenol oligomers. In this regard, reference is made to W. Carruthers, *Some Modern Methods of Organic Synthesis,* 3rd Ed., Cambridge University Press, 1986, and J. March, *Advanced Organic Chemistry,* 3rd Ed., John Wiley & Sons, 1985, van Rensburg et al., *J. Chem. Soc. Chem. Commun.* 24: 2705–2706 (Dec. 21, 1996), Ballenegger et al., (Zyma S A) European Patent 0096 007 B1, and documents in the References section below, all of which are hereby incorporated herein by reference.

The method of the present invention also provides a means for incorporation of a isotope label, e.g., deuterium and tritium, into polyphenol oligomers. For example, a polyphenol can be dissolved in $D_2O$ and $CD_3CN$, and gently heated in order to initiate H-D exchange (this reaction can also be carried out using $T_2O$ and $CH_3CN$ in order to incorporate a tritium into the molecule). Alternatively, deuterium or tritium may be incorporated using the methods of M. C. Pierre et al., *Tetrahedron Letters* 38, (32), 5639–5642 (1997) or E. Keihlmann et al., *Can. J. Chem.,* 26, 2431–2439 (1988). The incorporation of a deuterium or tritium atom in the polyphenol oligomer facilitates the determination of how polyphenol compounds may be metabolized following ingestion.

Advantageously, the method of the present invention also provides derivatized oligomers wherein at least one unprotected hydroxyl group of the polyphenol oligomer is derivatized using standard esterification or glycosylation techniques to form an ester or glycosyl ether derivative, respectively.

In addition, ester derivatives of the glycosyl ethers may be prepared by esterifying at least one hydroxyl group of the glycosyl. Exemplary derivatives include esters of caffeic, cinnamic, coumaric, ferulic, gallic, hydroxybenzoic and sinapic acids, and glycosyl ethers of glucose, galactose, xylose, rhamnose and arabinose.

Polyphenol oligomer esters may be prepared by treatment of the oligomer having a reactive hydroxyl moiety with an activated acid. As used herein, an activated acid is an organic acid having a carboxyl moiety that is activated toward reaction with an hydroxyl moiety. The activated acid may be a compound that can be isolated, such as an acid chloride, an acid anhydride, a mixed acid anhydride and the like, or may be formed in situ, for example by treatment of an acid with dicyclohexyl carbodiimide (DCC), carbonyl di-imidazole, and the like.

Polyphenol oligomer glycosides may be prepared by the methods described in Toshima, K.; Tatsuta, K. *Chem. Rev.,* 93, 1503–1531 (1993), Igarashi, K. *Adv. Carbohydr. Chem. Biochem.,* 34, 243 (1977) and D. Kahne et al., *J. Am. Chem. Soc.,* 11, 6881 (1989), or by treatment of a monomer using cyclodextrin glucanotransferase (EC 2.4.1.19, CGTase) according to the procedures described by Funayama et al. to produce a monomer glucoside (M. Funayama, H. Arakawa, R. Yamamoto, T. Nishino, T. Shin and S. Murao, *Biosci. Biotech. Biochem.,* 58, (5), 817–821 (1994)).

Examples 8 and 9 describe the preparation of a dimer bisgallate and trimer trisgallate, respectively. Their in vitro assessment (Example 15) against several human breast cancer cell lines showed activity equivalent to the pentamer. These results were surprising, since gallation of previously inactive procyanidin dimer and trimer substantially increased the antineoplastic activity of these oligomers. Thus, the gallation of oligomers produces compounds that are useful for the uses described in U.S. application Ser. No. 08/831,245, filed Apr. 2, 1997. Further, the following table lists exemplary examples of gallated oligomers useful for the uses described in U.S. application Ser. No. 08/831,245, filed Apr. 2, 1997.

Table: Gallated Procyanidin Oligomers

EC-3-O-galloyl-(4β→8)-EC-3-O-gallate
C-3-O-galloyl-(4α→8)-EC-3-O-gallate
C-3-O-galloyl-(4α→8)-C
EC-(4β→8)-EC-3-O-gallate
C-(4α→8)-EC-3-O-gallate
EC-3-O-galloyl-(4β→)-C
EC(4β→8)-EC-3-O-β-D-glucose-4,6-bisgallate
[EC-3-O-galloyl-(4β→8)]$_2$-EC-3-O-gallate
[EC-3-O-galloyl-(4β→8)]$_3$-EC-3-O-gallate
[EC-(4β→8)]$_4$-EC-3-O-gallate
[EC-(4β→8)]$_5$-EC-3-O-gallate
[EC-(4β→8)]$_6$-EC-3-O-gallate
[EC-(4β→8)]$_7$-EC-3-O-gallate
[EC-(4β→8)]$_8$-EC-3-O-gallate
[EC-(4β→8)]$_9$-EC-3-O-gallate
[EC-(4β→8)]$_{10}$-EC-3-O-gallate
[EC-(4β→8)]$_{11}$-EC-3-O-gallate The Examples which follow are intended as an illustration of certain preferred embodiments of the invention, and no limitation of the invention is implied. The skilled ark artisan will recognize many variations in these examples to cover a wide range of formulas and processing to rationally adjust the compounds of the invention for a variety of applications without departing from the spirit or scope of the invention.

In the following examples, (+)-catechin and (−)-epicatechin are exemplary polyphenol monomers used to demonstrate the method of the present invention and no limitation of the invention is implied. The (−)-epicatechin as used herein, may be obtained from commercial sources, or protected epicatechin may be prepared from protected (+)-catechin (Example 2).

EXAMPLE 1

Preparation of (2R, 3S, trans)-5,7,3',4'-Tetra-O-benzylcatechin

A solution of (+)-catechin (65.8 g, 226.7 mmol, anhydrous), dissolved in anhydrous dimethylformamide (DMF, 720 mL), was added dropwise, at room temperature over a period of 80 min, to a stirred suspension of sodium hydride, 60% in oil, (39 g, 975 mmol, 4.3 eq.) in DMF (180 mL). (S. Miura, et al., *Radioisotopes,* 32, 225–230 (1983)) After stirring for 50 min, the flask was placed in a −10° C. NaCl/ice bath. Benzyl bromide (121 mL, 1.02 mol, 4.5 eq.) was added dropwise within 80 min. and the brown reaction mixture warmed to room temperature, with stirring, overnight. The resulting reaction mixture was evaporated and the resulting candy-like solid was dissolved, with heating and stirring, in two portions of solvent each consisting of 200 mL of chloroform and 100 mL of water. The phases were separated, the aqueous phase extracted with chloroform (20 mL), and the combined organic phases washed with water (100 mL), dried over $MgSO_4$ and evaporated. The residue was purified by chromatography on silica gel (42×10 cm; ethyl acetate/chloroform/hexane 1:12:7) to provide, after evaporation and drying in vacuo, 85 g crude product, which was recrystallized from trichloroethylene (1.3 L) to provide 35.1 g (24%) of an off-white powder. $^1H$ NMR ($CDCl_3$) δ 7.47–7.25 (m, 20 H), 7.03 (s, 1 H), 6.95 (s, 2 H), 6.27, 6.21 (ABq, 2 H, J=2 Hz), 5.18 (s, 2 H), 5.17 (narrow ABq, 2 H), 5.03 (s, 2 H), 4.99 (s, 2 H), 4.63 (d, 1 H, J=8.5 Hz), 4.00 (m, 1 H), 3.11, 2.65 (ABq, 2 H, J=16.5 Hz, both parts d with J=5.5 and 9 Hz, resp.), 1.59 (d, 1 H, J=3.5 Hz); IR (film) 3440 (br), 1618, 1593, 1513, 1499, 1144, 1116, 733, 696 cm−1; MS m/z 650 (M+, 0.5%), 319, 181, 91.

Alternatively, the tetra-O-benzyl (+)-catechin may be prepared using the method described by H. Kawamoto et al, *Mokuzai Gakkaishi,* 37, (5) 488–493 (1991), using potassium carbonate and benzyl bromide in DMF. Partial racemization of catechin, at both the 2- and 3-positions, was observed by M.-C. Pierre et al., *Tetrahedron Letters,* 38, (32) 5639–5642 (1997).

EXAMPLE 2

Preparation of (2R)-5,7,3',4' Tetrakis(benzyloxy) flavan-3-one

Freshly prepared Dess-Martin periodinane (39.0 g, 92 mmol, prepared by the method of D. B. Dess and J. C. Martin, *J. Am. Chem. Soc.* 113, 7277–7287 (1991) and R. E. Ireland and L. Liu, *J. Org. Chem.* 58, 2899 (1993)), was added at room temperature, all at once, to a stirred solution of the tetra-O-benzyl catechin according to Example 1 (54.4 g, 83.8 mmol) in methylene chloride (420 mL). Within 1.5 h, approx. 30 mL of water-saturated methylene chloride was added dropwise to the reaction mixture to form a turbid amber-colored solution. (S. D. Meyer and S. L. Schreiber, *J. Org. Chem.,* 59, 7549–7552 (1994)) Twenty minutes thereafter, the reaction mixture was diluted with a saturated solution of $NaHCO_3$ (500 mL) and a 10% aqueous solution of $Na_2S_2O_5.5H_2O$ (200 mL). The phases were separated and the aqueous phase extracted with 50 mL of methylene chloride. The combined organic phases were filtered over silica gel (24×9 cm, chloroform/ethyl acetate 9:1). The eluate was evaporated and dried in vacuo to obtain 50.1 g (92%) of the ketone, which was purified by recrystallization from chloroform/ether: mp 144–144.5° C.; $[\alpha]_D$ +38.50°, $[\alpha]_{546}$ +48.70° (chloroform, c 20.8 g/L); $^1H$ NMR ($CDCl_3$) δ 7.45–7.26 (m, 20 H), 6.96 (s, 1 H), 6.88, 6.86 (ABq, 2 H, J=8 Hz, B part d with J=1.5 Hz), 6.35 (narrow ABq, 2 H), 5.24 (s, 1 H), 5.14 (s, 2 H), 5.10 (narrow ABq, 2 H), 5.02 (s, 2 H), 5.01 (s, 2 H), 4.63 (d, 1 H, J=8.5 Hz), 3.61, 3.45 (ABq, 2 H, J=21.5 Hz).

EXAMPLE 3

Preparation of 5,7,3',4'-Tetra-O-benzylepicatechin

A 1 M solution of lithium tri-sec-butylborohydride in tetrahydrofuran, herein after THF, (100 mL, L-Selectride®, sold by the Aldrich Chemical Co, Inc., Milwaukee, Wis.) was added, under an argon atmosphere, to a stirred, 0° C. solution of anhydrous LiBr (34.9 g, 402 mmol) in 100 mL anhydrous THF. The resulting mixture was cooled to −78° C., using an acetone/$CO_2$ bath, followed by dropwise addition of a solution of the flavanone according to Example 2 (50.1 g, 77.2 mmol) in 400 mL of anhydrous THF, over a period of 50 min. Stirring was continued at −78° C. for 135 min. The cooling bath was removed and 360 mL of 2.5 M aqueous NaOH was added to the reaction mixture. The reaction flask was placed in a room temperature water bath and a mixture of 35% aqueous $H_2O_2$ (90 mL) and ethanol (270 mL) was added over a period of 130 min. Stirring was continued overnight. Chloroform (700 mL) was added to dissolve the crystallized product, the phases were separated, the aqueous phase was extracted with $CHCl_3$ (50 mL), the combined organic phases were dried over $MgSO_4$, evaporated and dried in vacuo to provide 56.6 g of crude product. This material was dissolved in 600 mL of boiling EtOAc/ EtOH (2:3) and allowed to crystallize at room temperature, then in the refrigerator. The product was isolated by suction filtration, washed with 2×50 mL of cold (−20° C.) EtOAc/ EtOH (1:3), and dried in vacuo first at room temperature, then at 80° C. to obtain 35.4 g (70%) of a light-yellow solid. The evaporated mother liquor was filtered over $SiO_2$ (14×6.5 cm, $CHCl_3$, then $CHCl_3$/EtOAc 12:1), the eluate concentrated to 40 mL, and the residue diluted with 60 mL of ethanol, to obtain an additional 5.5 g (11%) of the O-benzylepicatechin as a yellowish solid: mp 129.5–130° C. (from EtOAc/EtOH); $[\alpha]_D$ −27.70, $[\alpha]_{546}$ −33.4° (EtOAc, c 21.6 g/L); $^1H$ NMR ($CDCl_3$) δ 7.48–7.25 (m, 20 H), 7.14 (s, 1 H), 7.00, 6.97 (ABq, 2 H, J=8.5 Hz, A part d with J=1.5 Hz), 6.27 (s, 2 H), 5.19 (s, 2 H), 5.18 (s, 2 H), 5.02 (s, 2 H), 5.01 (s, 2 H), 4.91 (s, 1 H), 4.21 (br s, 1 H), 3.00, 2.92 (ABq, 2 H, J=17.5 Hz, both parts d with J=1.5 and 4 Hz, resp.), 1.66 (d, I H, J=5.5 Hz); Anal. Calcd. for $C_{43}H_{38}O_6$: C, 79.36; H, 5.89. Found: C, 79.12: H, 5.99.

EXAMPLE 4

Preparation of (2R,3S,4S)-5,7,3',4'-Tetra-O-benzyl- 4-(2-hydroxyethoxy)epicatechin Ethylene glycol (6.4 mL, 115 mmol, 5.8 eq.) was added, at room temperature, with stirring, to a solution of the tetra-O-benzylepicatechin according to Example 3 (12.75 g, 19.6 mmol) in 130 mL of anhydrous methylene chloride, followed by addition of 2,3-dichloro-5,6-dicyano-1,4- benzoquinone (DDQ, 8.9 g, 39.2 mmol, 2.0 eq.), at one time, with vigorous stirring. (J. A. Steenkamp, et al., *Tetrahedron Letters,* 26, (25) 3045–3048 (1985)). After approximately 2 hours, 4-dimethylaminopyridine (DMAP, 4.8 g, 39.2 mmol) was added to the reaction mixture, resulting in the formation of a dark green precipitate. After stirring for an additional 5 minutes, 100 g of silica gel was added, and the mixture was concentrated under reduced pressure. The residue was placed on top of a silica gel column (11×6.5 cm) which was eluted with EtOAc/hexane (1:1), and the eluate was concentrated under reduced pressure. The resulting crude material was re-purified by chromatography on silica gel (39×10 cm, EtOAc/hexane (1:2), followed by EtOAc/hexane (2:3)) to provide, after evaporation and drying, in vacuo, 7.3 g (52%) of the benzyl-4-(2-hydroxy ethoxy) epicatechin, as a foam or solid, which was recrystallized from acetonitrile: mp 120–121° C.; $^1H$ NMR ($CDCl_3$) δ 7.48–7.26 (m, 20 H), 7.14 (d, J=1.5 Hz), 7.02, 6.97 (ABq, 2 H, J=8 Hz, A part d with J=1.5 Hz), 6.29, 6.26 (ABq, 2 H, J=2 Hz), 5.19 (s, 2 H), 5.17 (s, 2 H), 5.10 (s, 1 H), 5.08, 5.02 (ABq, 2 H, partially concealed), 5.00 (s, 2 H), 4.59 (d, 1 H, J=2.5 Hz), 3.95 (br, 1 H), 3.82–3.74 (m, 1 H), 3.72–3.57 (m, 3 H), 2.17 (br, 1 H), 1.64 (d, 1 H, J=5.5 Hz); IR (film) 3450 (br), 1616, 1592, 1512, 1152, 11 14, 735, 697 cm$^{-1}$. Anal. Calcd. for $C_{45}H_{42}O_8$: C, 76.04; H, 5.96. Found: C, 76.57; H, 6.02.

EXAMPLE 5

Preparation of O-Benzyl Epicatechin (4β→8) Oligomers

To a cold (0° C.), stirred solution of the benzyl-4-(2-hydroxy ethoxy) epicatechin according to Example 4 (3.28 g, 4.6 mmol) and the tetra-O-benzyl-epicatechin according to Example 3 (12.0 g, 18.4 mmol, 4 eq.) in anhydrous THF (40 mL) and anhydrous methylene chloride (50 mL), was added dropwise, in 10 min, titanium tetrachloride (4.6 mL of 1 M $TiCl_4$ in methylene chloride). (H. Kawamoto et al, *Mokuzai Gakkaishi,* 37, (5) 448–493 (1991)) The resulting amber-colored solution was stirred in the ice bath for 5 min, then at room temperature for 90 min. The reaction was terminated by addition of 30 mL of saturated aqueous $NaHCO_3$ and 100 mL of water (resulting pH: 8). The resulting mixture was extracted with methylene chloride (2×20 mL). The combined organic layers were washed with 50 mL of water, dried over $MgSO_4$, evaporated and dried in vacuo. The resulting glass deposited a pink solid upon dissolution in $CH_2Cl_2$ and standing at room temperature. The solid was filtered off, washed with 3×15 mL of $CH_2Cl_2$/hexane (1:1), and dried in vacuo to obtain 6.1 g of recovered tetra-O-benzylepicatechin. From the evaporated mother liquor, the oligomers were isolated by column chromatography on silica gel (45×5.2 cm). Elution with $CH_2Cl_2$/hexane/EtOAc (13:13:1) provided an additional 4.9 g of recovered tetra-O-benzylepicatechin, followed by 2.17 g of crude O-benzyl dimer. Elution of the dimer was completed using methylene chloride/hexane/EtOAc (10:10:1). Elution of 0.98 g of crude O-benzyl trimer and 0.59 g of higher oligomers was obtained using methylene chloride/hexane/EtOAc (8:8:1 to 6:6:1). The dimer and the trimer were further purified by preparative HPLC on a silica gel column, using ethyl acetate/hexane or ethyl acetate/isooctane as eluent. Peak detection was performed with a UV detector at 265 or 280 nm. Trimer: MS (MALDI-TOF, DHBA matrix) m/Z (M+H$^+$) 1949.4; calcd. for $C_{129}H_{111}O_{18}$: 1947.8; (M+Na$^+$) 1971.2; calcd. for $C_{129}H_{100}O_{18}Na$: 1969.8; (M+K$^+$) 1988.3; calcd. for $C_{129}H_{110}O_{18}K$: 1985.7.

EXAMPLE 6

Preparation of Epicatechin Dimer

To a solution of the O-benzyl-dimer according to Example 5 (22.3 mg, 17.2 μmol) in 0.5 mL of ethyl acetate was added sequentially, 2 mL of methanol and 7.2 mg of 10% Pd/C. The mixture was stirred under 1 bar of $H_2$ for 3 hours and filtered over cotton. The filtration residue was washed with methanol and the combined filtrates were evaporated. An NMR spectrum of the crude product indicated the presence of benzylated material. The procedure was therefore repeated, with the amount of catalyst increased to 17.5 mg and the time extended to 3.7 h. The crude polyphenol dimer (9.6 mg) was purified by preparative HPLC ($C_{18}$ reverse phase column water/methanol (85:15) with addition of 0.5% acetic acid, detection at 265 nm) to provide 4.5 mg (45%) of polyphenol dimer as an amorphous film. $^1$H NMR (300 MHz, acetone-$d_6$/$D_2O$ 3:1 (v/v), TMS) δ 7.19 (br, 1 H), 7.01 (overlapping s+br, 2 H), 6.86–6.65 (m, 4 H), 6.03 (br, 3 H), 5.10 (br, 1 H), 5.00 (br, 1 H), 4.69 (br, 1 H), 3.97 (s, 1 H), 2.92, 2.76 (br ABq, 2 H, J=17 Hz); MS (MALDI-TOF, DHBA matrix) m/z (M+K$^+$) 616.8; calcd. for $C_{30}H_{26}O_{12}K$: 617.1; (M+Na$^+$) 600.8; calcd. for $C_{30}H_{26}O_{12}Na$: 601.1.

EXAMPLE 7

Preparation of O-Benzyl Epicatechin Dimer Bisgallate

To a solution of tri-O-benzyl gallic acid (38 mg, 87 μmol, 5 eq.), DMF (1 μL) in methylene chloride (0.6 mL), was added oxalyl chloride (15 μL, 172 μmol, 10 eq.). The resulting reaction mixture was stirred at room temperature for approximately 1 hour, evaporated and dried in vacuo to provide tri-O-benzyl galloyl chloride. A solution of the O-benzyl-dimer according to Example 5 (22.5 mg, 17.3 μmol) in anhydrous pyridine (0.5 mL) was added to the crude galloyl chloride at room temperature, and the resulting mixture was stirred for 44.5 h. After addition of 20 μL of water, stirring was continued for 2.5 h, followed by addition of 10 mL of 5% HCl. The resulting mixture was extracted with methylene chloride (3×5 mL), the combined organic phases were dried over $MgSO_4$, evaporated and purified by filtration over silica gel using with EtOAc/$CHCl_3$ (1:19). Concentration of the eluate and drying in vacuo yielded 36.0 mg (97%) of the O-benzyl dimer bisgallate as a colorless film: [α]$_D$ −53.3°, [α]$_{546}$ −65.6° ($CH_2Cl_2$, c 15.7 g/L); IR (film) 1720, 1591, 1498, 1428, 1196, 1112, 736, 696 cm$^{-1}$; MS (MALDI-TOF, DHBA matrix) m/z (M+K$^+$) 2181.8; calcd. for $C_{142}H_{118}O_{20}K$: 2181.8; (M+Na$^+$) 2165.9; calcd. for $C_{142}H_{118}O_{20}Na$: 2165.8.

EXAMPLE 8

Preparation of Epicatechin Dimer Bisgallate 9

To a solution of the O-benzyl dimer bisgallate according to Example 7 (33.8 mg, 15.8 μmol) in 4 mL of THF was added sequentially 4 mL of methanol, 0.2 mL of water, and 42 mg of 20% Pd(OH)$_2$/C. The mixture was stirred under 1 bar of $H_2$ for 75 minutes and filtered over cotton. The filtration residue was washed with 2.2 mL of methanol/$H_2O$ (10:1) and the combined filtrate was concentrated under reduced pressure to provide 14.2 mg of yellowish, amorphous crude product. A 7.2 mg aliquot was purified by preparative HPLC (silica gel, ethyl acetate/hexane; detection at 280 nm) to yield 5.0 mg (71%) of the polyphenol dimer bisgallate as a turbid pinkish glass from which small amounts of ethanol and acetic acid could not be removed: $^1$H NMR (acetone-$d_6$/$D_2O$ 3:1 v/v, TMS, most signals broad) δ 7.08 (s, 2 H, sharp), 7.1–6.7 (m, 7 H), 6.66 (d, 1 H, sharp, J=8 Hz), 6.17 (s, 1 H), 5.94 (s, 2 H), 5.70 (s, 1 H), 5.49 (s, 1 H), 5.44 (s, 1 H), 4.9 (very br, 1 H), 4.80 (s, 1 H), 3.08, 2.88 (ABq, 2 H, J=17 Hz, A part d, J=4 Hz); MS (MALDI-TOF, DHBA matrix) m/z (M+Na$^+$) 904.9; calcd. for $C_{44}H_{34}O_{20}Na$: 905.2.

EXAMPLE 9

Preparation of O-Benzyl Epicatechin Trimer Trisgallate

Using the procedure described in Example 7, O-benzyl trimer trisgallate was obtained from the O-benzyl trimer according to Example 5 in 78% yield after purification by HPLC (conditions: silica gel, ethyl acetate/hexane, 280 nm); $^1$H NMR: extremely complex; IR (film) 3031, 1719, 1594, 1498, 1428, 1116, 735, 696 cm$^{-1}$.

EXAMPLE 10

Preparation of Epicatechin Trimer Trisgallate

Using the procedure described in Example 8, polyphenol trimer trisgallate was obtained from the O-benzyl trimer trisgallate according to Example 9 in 60% yield after purification by HPLC. ($C_{18}$ reverse phase gradient of 15–25% B in A, where A is 0.5 vol. % acetic acid (AcOH) in water and B is 0.5% AcOH in ethanol; 280 nm); $^1$H NMR (300 MHz, $D_2O$/acetone-$d_6$ 1:3 (v/v)) δ 7.10 (s, 2 H), 7.1–6.88 (m, 7 H), 6.82–6.70 (m, 3 H), 6.68–6.60.

EXAMPLE 11

Preparation of 8-Bromo-5,7,3',4'-tetra-O-benzylepicatechin

To a solution of 116 mg (178 μmol) of tetra-O-benzylepicatechin, according to Example 3, in 4 mL of anhydrous $CH_2Cl_2$ was added with ice cooling and stirring 32 mg (180 μmol) of N-bromosuccinimide. Stirring at 0° C. was continued for 100 min, the solution was concentrated, and the residue was purified by chromatography on silica gel (15×1.8 cm) with $CHCl_3$/EtOAc (25:1). Crystallization from $CHCl_3$/ethanol gave 110 mg (85%) of a colorless, cotton-like solid. Mp 137.5° C.; $[\alpha]_D$ −50.4°, $[\alpha]_{546}$ −60.7° (c 17.3 g/L, EtOAc); $^1$H NMR (300 MHz, $CDCl_3$, TMS) δ 7.5–7.25 (m, 20 H), 7.23 (d, 1 H, J=1.5 Hz), 7.03, 6.98 (ABq, 2 H, J=8.5 Hz, A part d with J=1 Hz), 6.25 (s, 1 H), 5.22 (s, 2 H), 5.19 (s, 2 H), 5.11 (s, 2 H), 5.02, 4.96 (ABq, 2 H, J=9 Hz), 4.98 (s, 1 H), 4.27 (br s, 1 H), 3.04, 2.90 (ABq, 2 H, J=17.5 Hz, both parts d with J=1.5 and 4 Hz, resp.), 1.58 (d, 1 H, J=4.5 Hz); $^{13}$C NMR (75 MHz, $CDCl_3$) δ 156.86, 154.79, 151.65, 149.09, 148.73, 137.31, 137.15, 136.77, 136.72, 130.82, 128.67, 128.65, 128.58, 128.56, 128.09, 127.98, 127.87, 127.50, 127.31, 127.25, 127.13, 118.91, 115.17, 113.07, 102.85, 93.07, 78.62, 71.35, 71.20, 70.31, 65.92, 28.00; IR (mineral oil suspension) 3571, 1606, 1581, 1518, 1184, 1129, 771, 732, 694 cm$^{-1}$; MS m/z 399/397 (1/1%), 332 (1% 0), 181 (8%), 91 (100%). Anal. calcd. for $C_{43}H_{37}O_6Br$: C, 70.78; H, 5.11. Found: C, 70.47; H, 5.10.

EXAMPLE 12

Preparation of O-Benzyl Epicatechin Tetramer

The O-benzyl epicatechin trimer according to Example 5 is brominated in position 8 of the top epicatechin moiety using the procedure of Example 10. The resulting bromo derivative is reacted with 5,7,3',4'-tetra-O-benzyl-4-(2-hydroxyethoxy)epicatechin according to Example 5 to yield a mixture of tetramers having the fourth epicatechin moiety attached to the 6-positions predominantly of the bottom and center epicatechin moieties, as well as higher oligomers. The desired intermediate,

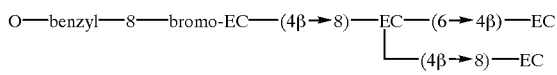

is isolated by preparative HPLC as in Example 10. The purified intermediate is debrominated by treatment of its THF solution at low temperature, preferably at −78° C., with an excess of an alkyllithium, preferably n- or tert-butyllithium, and protonation of the resulting solution or suspension of the lithiated protected branched tetramer by addition of a weak proton acid, such as water or an alcohol.

EXAMPLE 13

Preparation of O-Benzyl Epicatechin Tetramer Tetragallate

Using the procedure described in Example 7, the O-benzyl epicatechin tetramer tetragallate is obtained from the O-benzyl epicatechin tetramer according to Example 12.

EXAMPLE 14

Preparation of Epicatechin Tetramer Trisgallate

Using the procedure described in Example 8, the epicatechin tetramer tetragallate is obtained from the O-benzyl epicatechin tetramer tetragallate according to Example 13.

EXAMPLE 15

Cytotoxic Activity

Figure 1B:
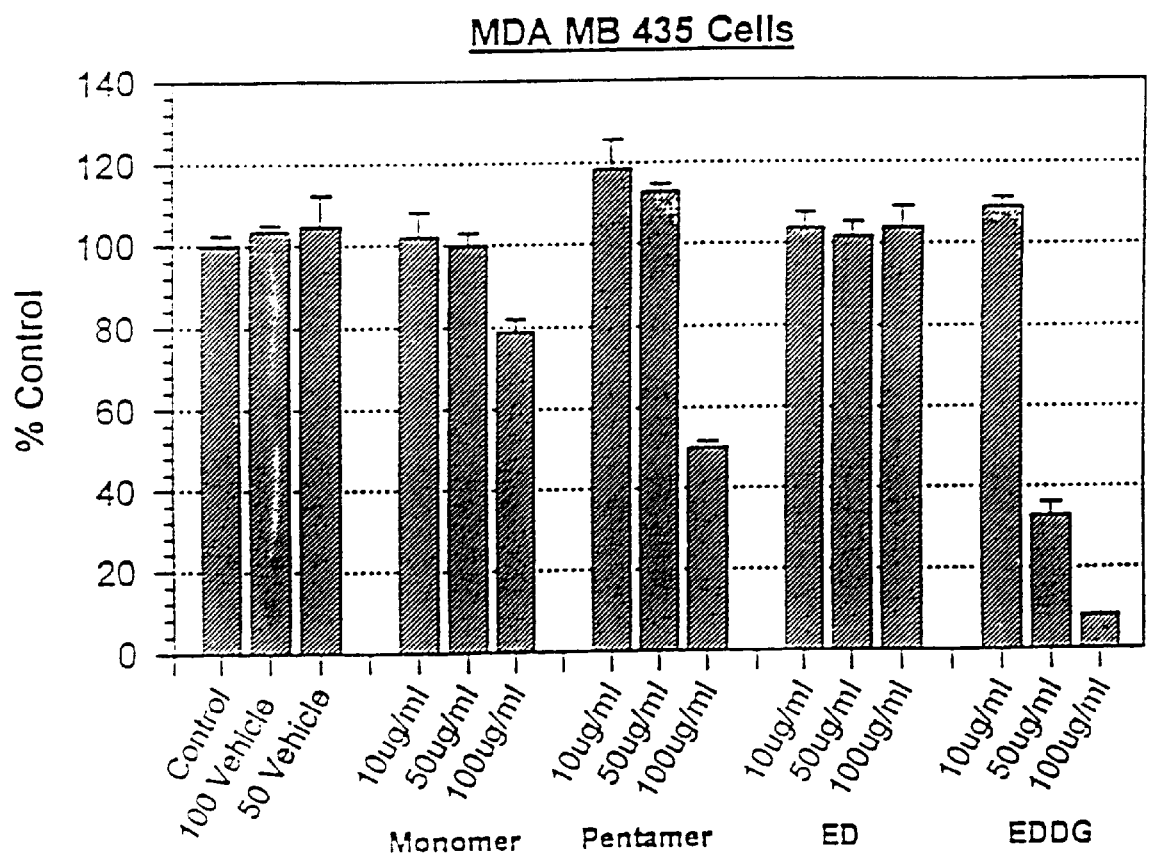
FIG. 1(b) is a bar graph showing the dose-response relationship between the control (solvent vehicle), monomer (epicatechin), pentamer (purified by preparative HPLC), ED (synthetic epicatechin dimer (EC-(4β→8)-EC)), and EDDG (synthesized epicatechin dimer bisgallate (EC-3-O-galloyl-(4β→8)-EC-3-O-gallate)) against the human breast cancer cell line MDA MB 435 at various μg/mL concentrations.
Figure 1C:
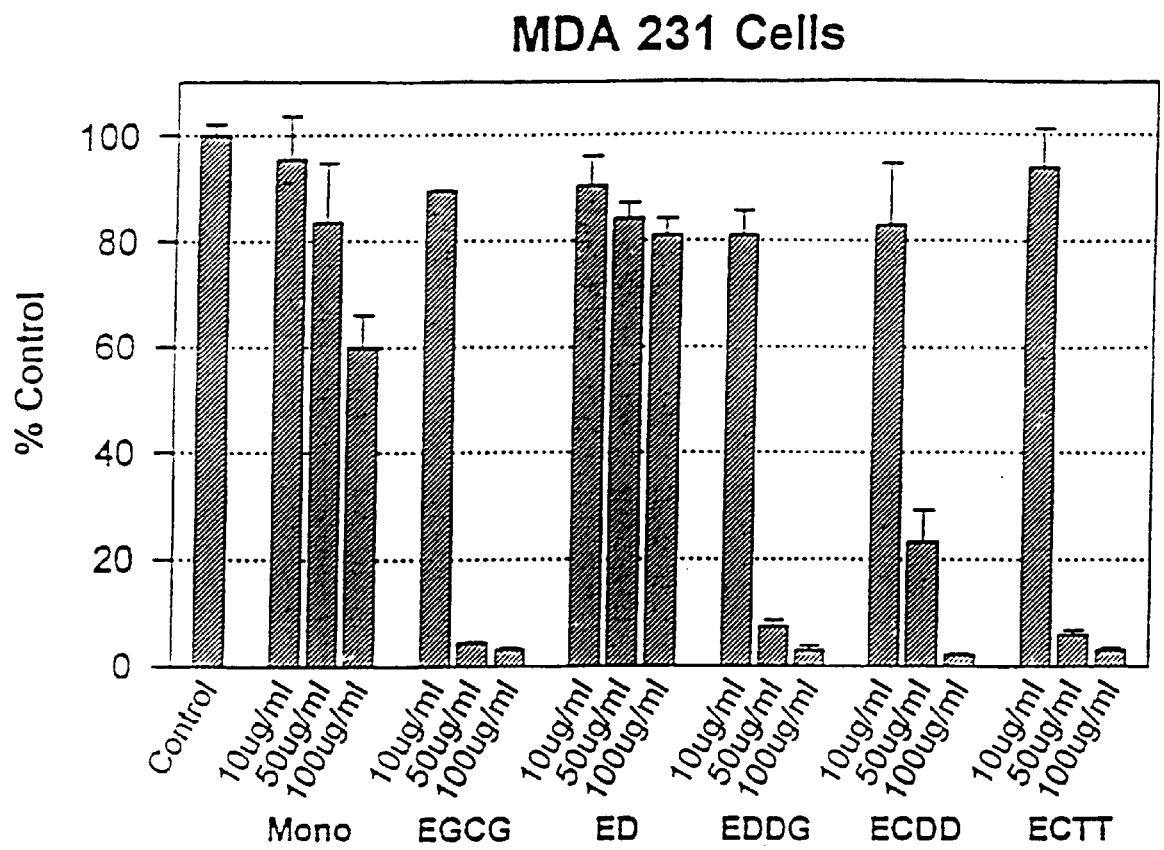
FIG. 1(c) is a bar graph showing the dose-response relationship between the control (solvent vehicle), monomer (epicatechin), EGCG (epigallocatechin gallate from Sigma), ED (synthesized epicatechin dimer (EC-(4β→8)-EC)), EDDG (synthesized epicatechin dimer bisgallate (EC-3-O-galloyl-(4β→8)-EC-3-O-gallate)), ECDD (repeated synthesis of epicatechin dimer bisgallate (EC-3-O-galloyl-(4β→8)-EC-3-O-gallate)), and ECTT (synthesized epicatechin trimer trisgallate ([EC-3-O-galloyl-(4β→8)]$_2$-EC-3-O-gallate)) against the human breast cancer cell line MDA 231 at various μg/mL concentrations.
Figure 1D:
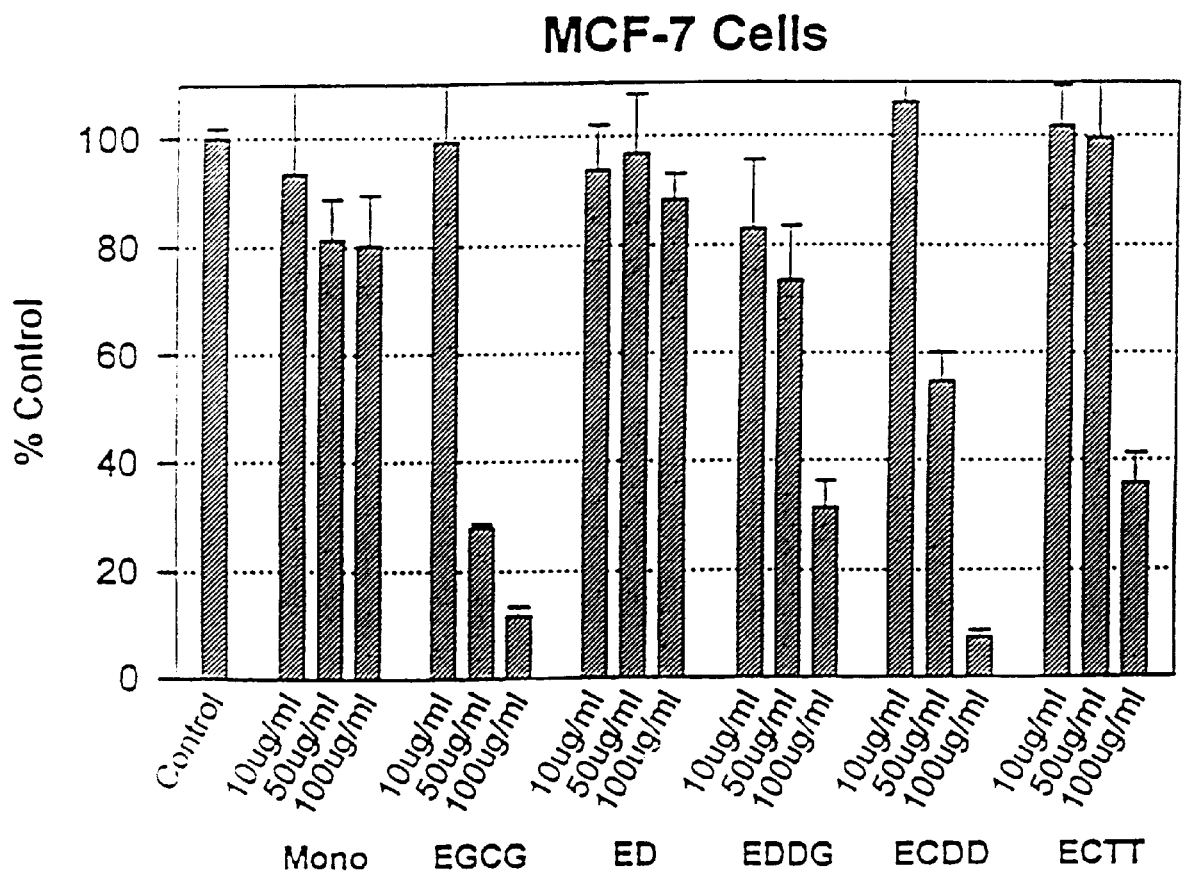
FIG. 1(d) is a bar graph showing the dose-response relationship between the control (solvent vehicle), monomer (epicatechin), EGCG (epigallocatechin gallate from Sigma), ED (synthesized epicatechin dimer (EC-(4β→8)-EC)), EDDG (synthesized epicatechin dimer bisgallate (EC-3-O-galloyl-(4β→8)-EC-3-O-gallate)), ECDD (repeated synthesis of epicatechin dimer bisgallate (EC-3-O-galloyl-(4β→8)-EC-3-O-gallate)), and ECTT (synthesized epicatechin trimer trisgallate ([EC-3-O-galloyl-(4β→8)]$_2$-EC-3-O-gallate)) against the human breast cancer cell line MCF-7 at various μg/mL concentrations.

The epicatechin dimer bisgallate (abbreviated ECDG) and epicatechin trimer trisgallate (abbreviated ECTG) were screened for activity against certain breast cancer cell lines, and the results are presented graphically in FIGS. 1(a)–(d).

All human tumor cell lines were obtained from the American Type Culture Collection. Cells were grown as monolayers in IMEM containing 10% fetal bovine serum without antibiotics. The cells were maintained in a humidified, 5% $CO_2$ atmosphere at 37° C.

After trypsinization, the cells were counted and adjusted to a concentration of 1,000–2,000 cells per 100 mL. Cell proliferation was determined by plating the cells (1,000–2,000 cells/well) in a 96 well microtiter plate. After addition of 100 μL cells per well, the cells were allowed to attach for 24 hours. At the end of the 24 hour period, various polyphenol derivatives were added at different concentrations to obtain dose response results. The polyphenols were dissolved in media at a 2 fold concentration and 100 μL of each solution was added in triplicate wells. On consecutive days, the plates were stained with 50 μL crystal violet (2.5 g crystal violet dissolved in 125 mL methanol, 375 mL water), for 15 min. The stain was removed and the plate was gently immersed into cold water to remove excess stain. The washings were repeated two more times, and the plates allowed to dry. The remaining stain was solubilized by adding 100 μL of 0.1 M sodium citrate/50% ethanol to each well. After solubilization, the number of cells were quantitated on an ELISA plate reader at 540 nm (reference filter at 410 nm).

Cancer cell line growth at the end of four days was plotted as the percent growth of the control and is shown in FIGS. 1(a)–(d) as bar graphs. Error bars represent +/− standard deviation of three replicate measurements. The data indicated that the monomer (epicatechin) and synthetic epicatechin dimer showed no cytotoxicity against the breast cancer cell lines investigated. However, the synthetic epicatechin dimer bisgallate and synthetic epicatechin trimer trisgallate elicited a cytotoxic effect equivalent to the pentamer and/or epigallocatechin gallate, especially at higher dosages.

It was surprisingly found that the dimer bisgallate and trimer trisgallate exhibited greater antineoplastic activity when compared to the underivatized dimer and trimer. These results indicate that gallation of the previously inactive cocoa procyanidin oligomers substantially increases the antineoplastic activity of the compounds. Thus, gallation of the dimer provides a compound which is useful for the uses as described in U.S. application Ser. No. 08/831,245 filed Apr. 2, 1997.

What is claimed is:

1. A process for the preparation of a procyanidin (4→8) dimer, comprising the steps of:

(a) protecting each phenolic hydroxyl group of an epicatechin monomer to form a protected epicatechin monomer, (b) oxidizing the 4-position of the protected epicatechin monomer to form a protected dimer derivatized at the 4-position with a $C_2$–$C_6$ alkoxy group having a terminal hydroxy group;

(c) coupling the derivatized, protected epicatechin monomer with a protected catechin monomer or protected epicatechin monomer to form a protected procyanidin (4→8) dimer; and (d) deprotecting the protected procyanidin (4→8) dimer.

2. A process for the preparation of a procyanidin (4→8) oligomer, having n monomeric units, where n is 3 to 18, which process comprises the steps of:

(a) protecting each phenolic hydroxyl group of an epicatechin monomer to form a protected epicatechin monomer;

(b) oxidizing the 4-position of the protected epicatechin monomer to form a protected epicatechin monomer derivatized at the 4-position with a $C_2$–$C_6$ alkoxy group having a terminal hydroxyl group;

(c) coupling the derivatized, protected epicatechin monomer with a protected catechin monomer or a protected epicatechin monomers to form a protected procyanidin (4→8) dimer;

(d) coupling additional protected epicatechin monomer(s) derivatized at the 4-position with a $C_2$–$C_6$ alkoxy group having a terminal hydroxyl group, or additional protected catechin monomers derivatized at the 4-position with a $C_2$–$C_6$ alkoxy group having a terminal hydroxyl group to form a protected procyanidin (4→8) oligomer having the desired number of monomeric units; and (e) deprotecting the protected procyanidin (4→8) oligomer.

3. A process for the preparation of a procyanidin (4→6) dimer, comprising the steps of:

(a) protecting each phenolic hydroxyl group of an epicatechin monomer to form a protected epicatechin monomer;

(b) oxidizing the 4-position of the protected epicatechin monomer to form a protected epicatechin monomer derivatized at the 4-position with a $C_2$–$C_6$ alkoxy group having a terminal hydroxyl group;

(c) blocking the 8-position of a protected catechin monomer or of a protected epicatechin monomer by introducing a halogen;

(d) coupling the derivatized, protected epicatechin monomer with the blocked, protected catechin monomer or the blocked, protected epicatechin monomer to form a blocked, protected procyanidin (4→6) dimer; and (e) deblocking and deprotecting the procyanidin (4→6) dimer to form the (4→6) dimer.

4. A process for the preparation of a procyanidin (4→6) oligomer, having n monomeric units, where n is 3–18, which process comprises the steps of:

(a) protecting each phenolic hydroxyl group of an epicatechin monomer to form a protected epicatechin monomer;

(b) oxidizing the 4-position of the blocked, protected epicatechin monomer to form a protected epicatechin monomer derivatized at the 4-position with a $C_2$–$C_6$ alkoxy group having a terminal hydroxyl group;

(c) blocking the 8-position of a protected catechin monomer or of a protected epicatechin monomer by introducing a halogen;

(d) coupling the derivatized, blocked, protected epicatechin monomer with a blocked, protected catechin monomer or with a blocked, protected epicatechin monomer to form a blocked, protected procyanidin (4→6) dimer;

(e) coupling the blocked, protected epicatechin dimer with additional blocked, protected epicatechin monomers (a) derivatized at the 4-position with a $C_2$–$C_6$ alkoxy group having a terminal hydroxyl group or with additional blocked, protected catechin monomer(s) derivatized at the 4-position with a $C_2$–$C_6$ alkoxy group having a terminal hydroxyl group to form a blocked, protected procyanidin (4→6) oligomer having the desired number of monomeric units; and (f) deblocking and deprotecting the blocked, protected procyanidin (4→6) oligomer.

5. The process of claims 1, 2, 3, or 4, or wherein the phenolic hydroxyl groups are protected with benzyl protecting groups.

6. The process of claims 1, 2, 3, or 4, wherein the deprotecting is carried out by hydrogenating the protected phenolic hydroxyl groups.

7. The process of claims 1, 2, 3, or 4, wherein a protic acid or Lewis acid is used in the coupling step.

8. The process of 7, wherein the protic acid is hydrochloric acid.

9. The process of 7, wherein the Lewis acid is selected from the group consisting of: titanium tetrahalides, aluminum trihalides, boron trihalides and triaryl silyls.

10. The process of claims 1, 2, 3, or 4, wherein the dimer or oligomer is esterified at the C-3 position(s) to form a derivative.

11. The process of claim 10, wherein the derivative is formed using an acid selected from the group consisting of: caffeic, cinnamic, coumaric, ferulic, gallic, hydroxybenzoic and sinapic.

12. The process of claims 1, 2, 3, or 4, wherein the 4-alkoxy derivative is a $C_2$–$C_6$ alkoxy group.

13. The process of claim 12, wherein the $C_2$–$C_6$ alkoxy is 2-hydroxyethoxy.

14. The process of claims 1, 2, 3, or 4, wherein the 4-alkoxy derivative is formed by oxidizing the 4-position of the first protected epicatechin monomer using ethylene glycol.

15. The process according to claims 1, 2, 3, or 4, wherein n is 4 to 18.

16. The process according to claim 15, wherein n is 5 to 12.

17. The process of claims 1, or 3, further comprising the step of purifying the protected procyanidin dimer by preparative high pressure liquid chromatography before additional coupling of the dimer with the protected monomer or the blocked protected monomer.

* * * * *

UNITED STATES PATENT AND TRADEMARK OFFICE
CERTIFICATE OF CORRECTION

PATENT NO. : 6,207,842 B1
DATED : March 27, 2001
INVENTOR(S) : Romanczyk, Jr. et al.

It is certified that error appears in the above-identified patent and that said Letters Patent is hereby corrected as shown below:

Column 33,
Line 44, "Example 5" should read -- Example 4 --.

Column 34,
Line 67, "protected dimer" should read -- protected monomer --.

Column 35,
Line 58, step (b) "the blocked, protected" should read -- the protected --.

Column 36,
Line 4, step (d) "derivatized, blocked, protected" should read -- derivatized, protected --.
line 11, "(a)" should be deleted.

Signed and Sealed this

Nineteenth Day of August, 2003

JAMES E. ROGAN
*Director of the United States Patent and Trademark Office*